United States Patent [19]

Takayama et al.

[11] Patent Number: 5,372,124
[45] Date of Patent: Dec. 13, 1994

[54] TREATING INSTRUMENT

[75] Inventors: Shuichi Takayama, Tokyo; Akio Nakada, Kanagawa; Yasukazu Tatsumi, Tokyo; Takeaki Nakamura, Tokyo; Tatsuya Yamaguchi, Tokyo; Yasuhiro Ueda, Tokyo; Hideyuki Adachi, Tokyo; Masakazu Gotanda, Kanagawa; Koji Fujio, Tokyo; Katsunori Sakiyama, Tokyo; Masaaki Hayashi, Tokyo, all of Japan

[73] Assignee: Olympus Optical Co., Ltd., Tokyo, Japan

[21] Appl. No.: 864,521

[22] Filed: Apr. 7, 1992

[30] Foreign Application Priority Data

Apr. 10, 1991 [JP] Japan .................. 3-077811
Dec. 6, 1991 [JP] Japan .................. 3-323151
Mar. 17, 1992 [JP] Japan .................. 4-060679

[51] Int. Cl.⁵ .............. A61B 1/00; A61B 10/00; B25J 15/00
[52] U.S. Cl. ...................... 128/4; 128/751; 606/205; 901/36; 414/4
[58] Field of Search ............. 606/205–209, 606/177–178, 169–170; 128/4, 180, 772, 657, 20, 751, 749; 604/176–178, 180; 901/31, 32, 36–38; 310/325, 328, 311; 318/115, 116, 135; 294/86 H, 104; 414/4

[56] References Cited

U.S. PATENT DOCUMENTS

| | | | |
|---|---|---|---|
| 2,082,782 | 6/1937 | Allen | 604/176 X |
| 3,227,290 | 1/1966 | Lemelson | 901/32 X |
| 4,427,000 | 1/1984 | Ueda | 128/6 |
| 4,468,162 | 8/1984 | Kuromoto | 414/4 |
| 4,509,517 | 4/1985 | Zibelin | 128/319 |
| 4,607,620 | 8/1986 | Storz | |
| 4,655,673 | 4/1987 | Hawkes | 901/33 X |
| 4,727,278 | 2/1988 | Staufenberg, Jr. et al. | 310/328 |
| 4,944,093 | 7/1990 | Falk | 606/205 X |
| 4,982,727 | 1/1991 | Sato | 128/4 |
| 4,999,536 | 3/1991 | Toda | 310/328 X |
| 5,074,311 | 12/1991 | Hasson | 606/170 X |

FOREIGN PATENT DOCUMENTS

| | | | |
|---|---|---|---|
| 56-112221 | 9/1981 | Japan . | |
| 62-164009 | 10/1987 | Japan . | |
| 0770790 | 10/1980 | U.S.S.R. | 294/86.4 |
| 0867647 | 9/1981 | U.S.S.R. | 294/86.4 |

Primary Examiner—Richard J. Apley
Assistant Examiner—John P. Leubecker
Attorney, Agent, or Firm—Frishauf, Holtz, Goodman & Woodward

[57] ABSTRACT

A treating instrument for medical treatment, comprises an insertion section to be inserted into a body cavity of a patient, biopsying forceps provided at a distal end of the insertion section, a pair of cups provided at the forceps, a grip member connected to an operator-end side of the insertion section; a drive unit provided on the distal end of the insertion section and generating a drive force for the cups, a conduction circuit for carrying electric current through the drive unit, and an operation switch interposed at lead wires of the conduction circuit.

2 Claims, 17 Drawing Sheets

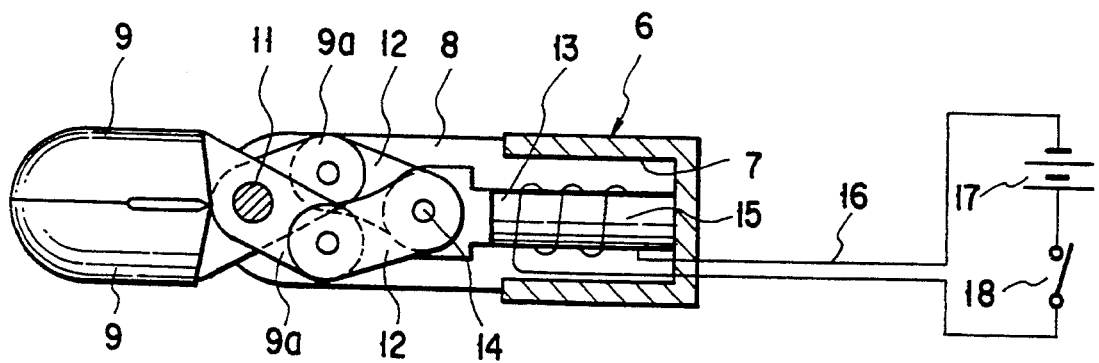
F I G. 3A
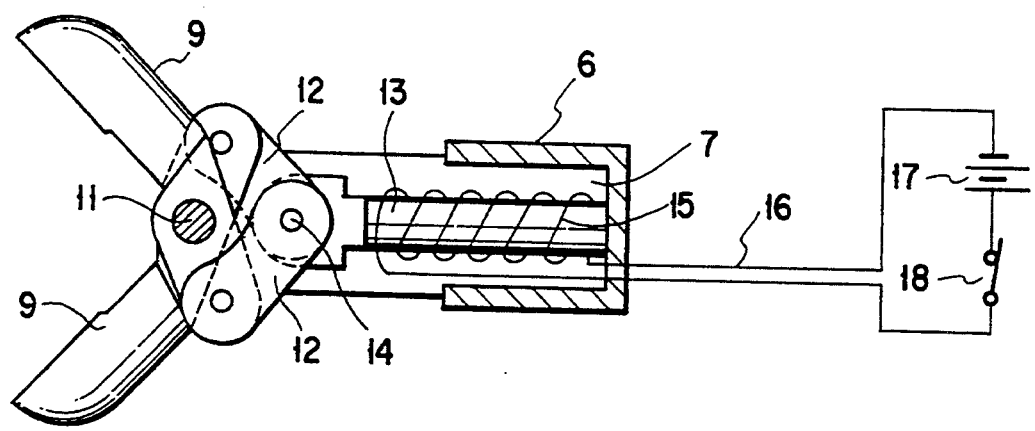
F I G. 3B

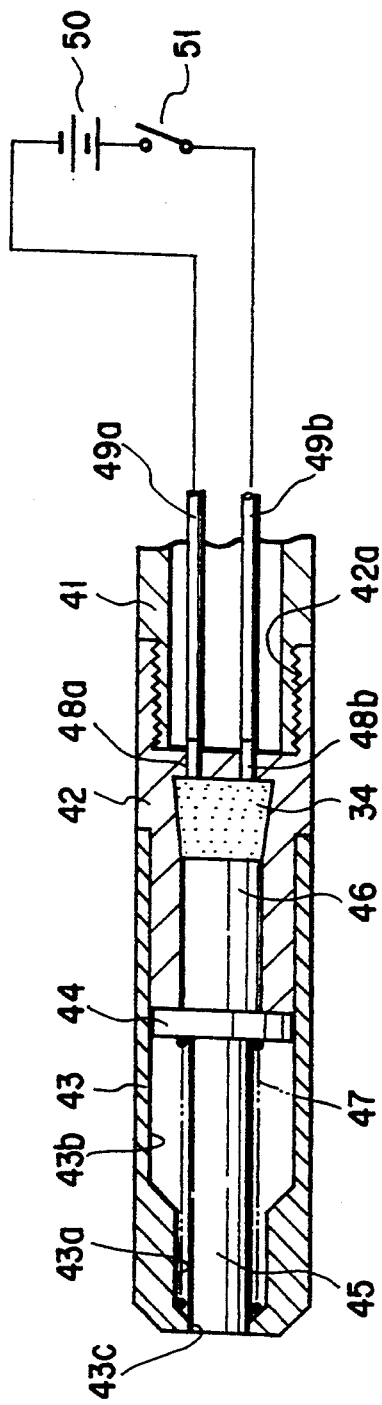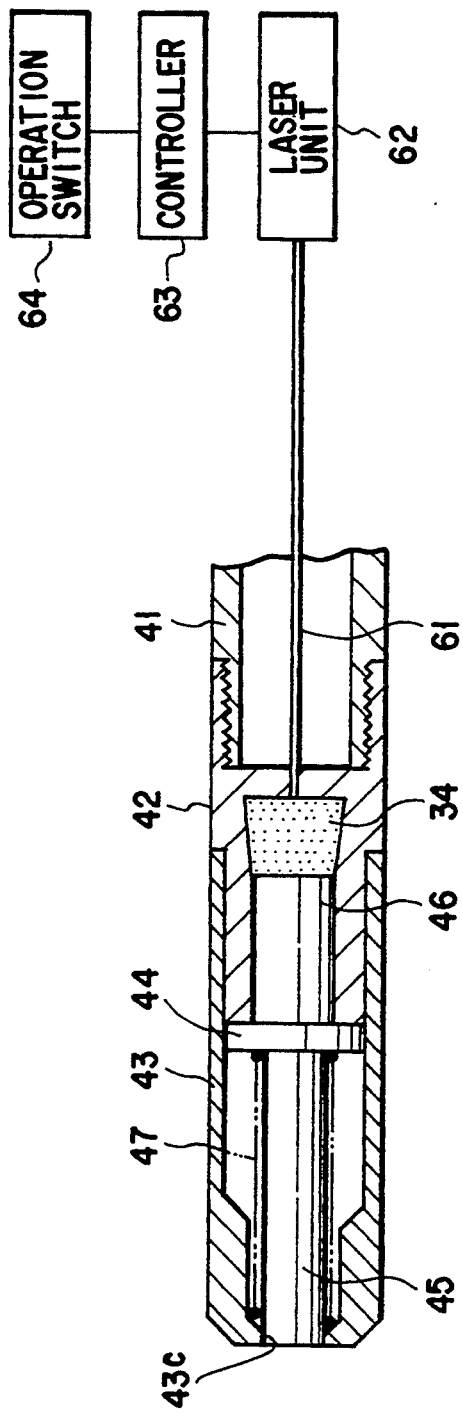
FIG. 5A
FIG. 5B

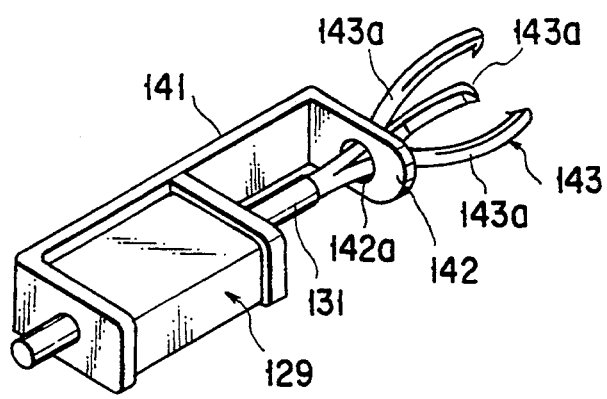
F I G. 13
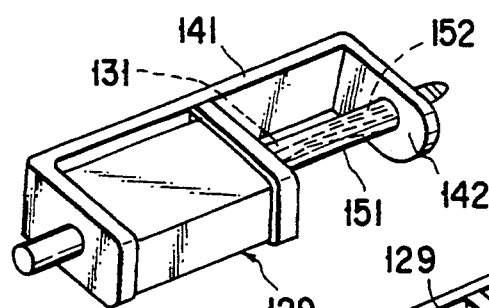
F I G. 14A
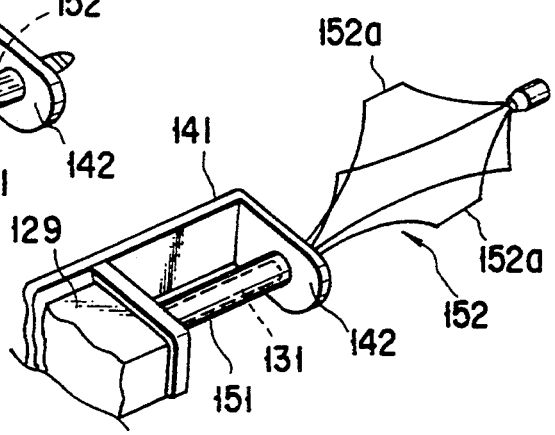
F I G. 14B
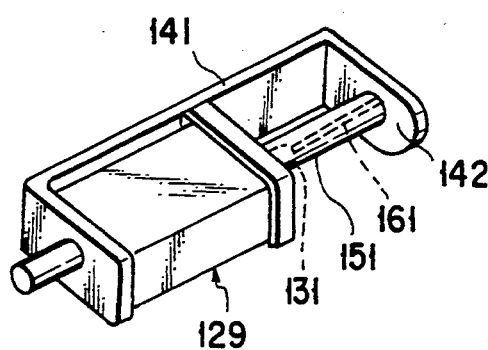
F I G. 15A
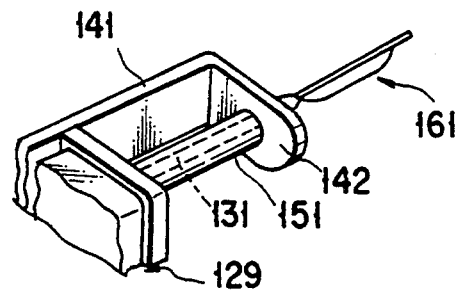
F I G. 15B

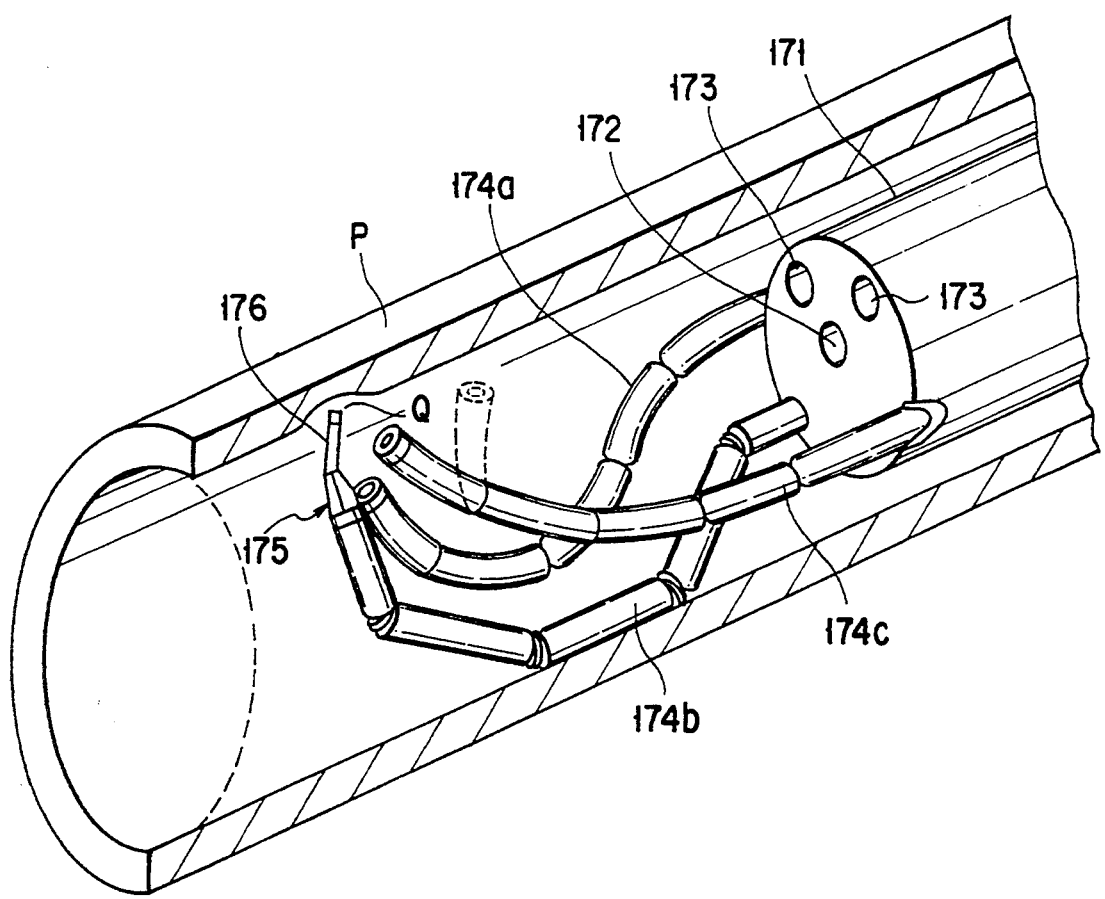
F I G. 16

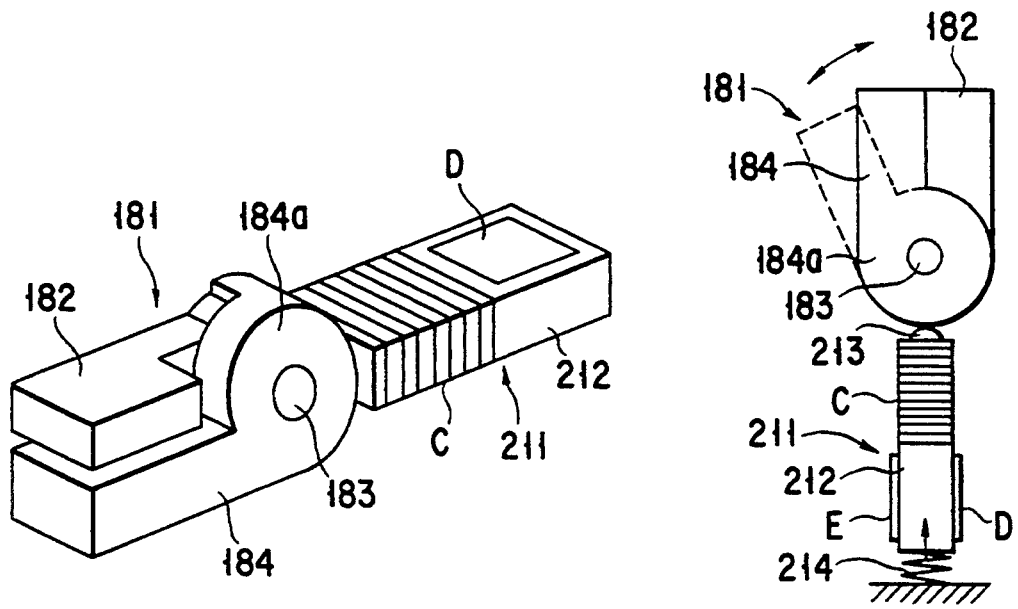
F I G. 20A     F I G. 20B
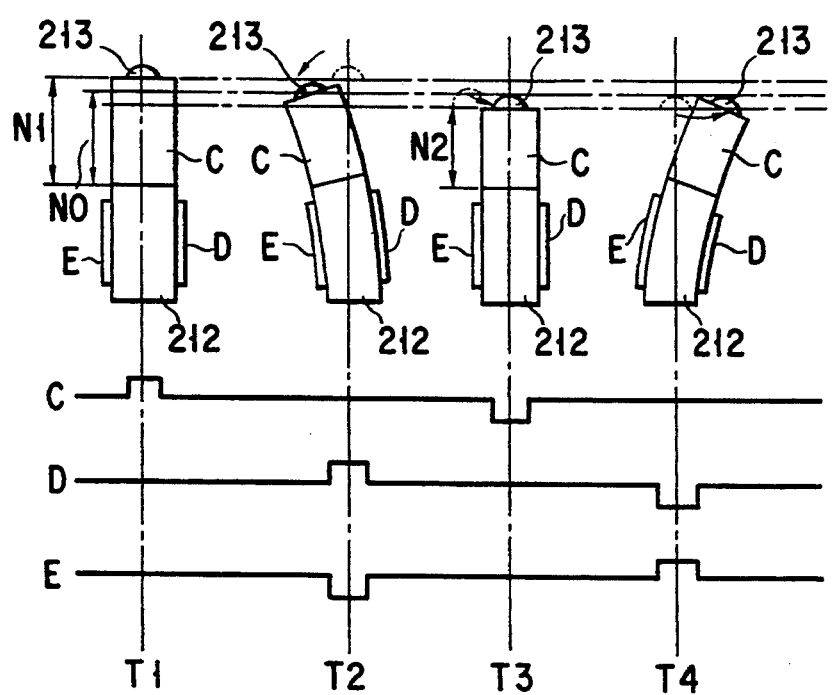
F I G. 21

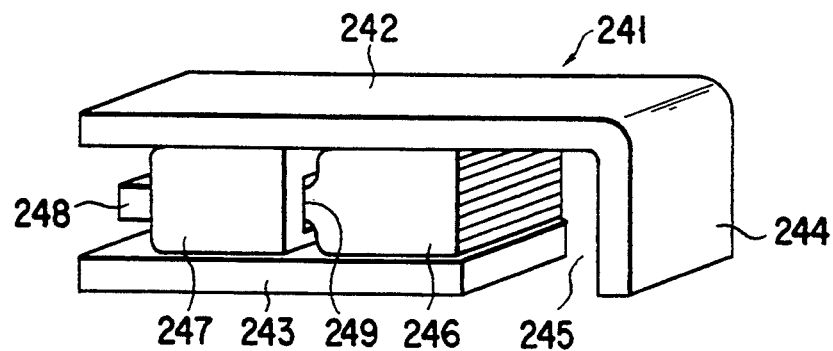
F I G. 25
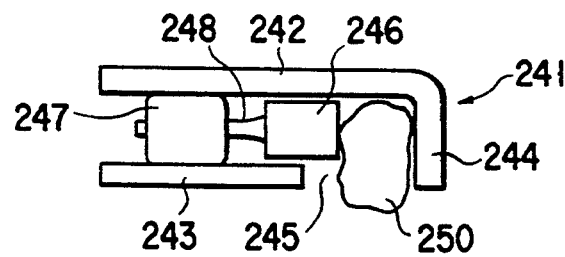
F I G. 26
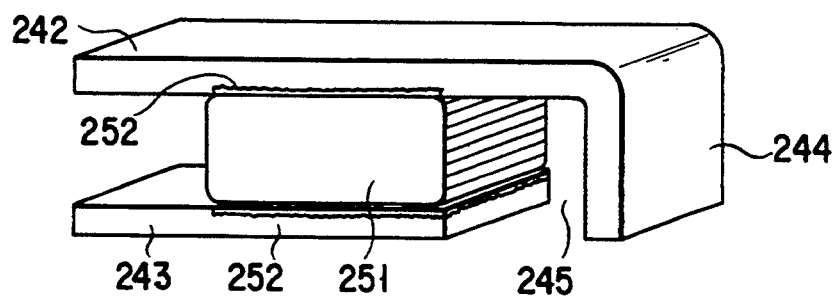
F I G. 27

TREATING INSTRUMENT

BACKGROUND OF THE INVENTION

1. Field of the Invention

The present invention relates to a treating instrument inserted into, for example, a body cavity of a patient for medical treatment or into a given cavity of a pipe or duct for treatment or repair.

2. Description of the Related Art

For example, Published Unexamined Japanese Patent Application 56-112221 and Published Unexamined Japanese Utility Model 62-164009 disclose biopsying forceps as one form of a treating instrument for an endoscope. In the forceps disclosed, a pair of openable/closable biopsying cups are mounted on the distal end of a lengthy insertion sheath. The cups are connected to the forward end of operation wire means inserted through the insertion sheath.

The operation wire means is connected at a base end to an operation mechanism on the operator's side of the forceps. In the forceps, biopsying cups are opened and closed by the operation of an operation mechanism on the operator-end side and hence a remote-controlled push/pull operation.

In the conventional treating instrument for an endoscope, an operation force of the operation mechanism is transmitted by operating wire means to the biopsying cups on a distal end of the lengthy sheath. It is necessary to use an operation wire means of a proper thickness enough strong to transmit an operative mechanical drive force to the cups. In the conventional treating instrument for an endoscope, however, there is a limit on the diameter narrowing of the insertion sheath, failing to reduce the diameter of the insertion sheath to a minimum possible extent.

Further, a mechanism is required which can transmit a drive force which arises from the actuated operation wire means, as a mechanical motion, to the treating member, such as the biopsying forceps. This involves a complex structure on the distal end of the insertion sheath.

Since the cups are opened or closed by the manually-controlled operation of the operation wire means, such opening/closing operation appreciably differ from operator to operator. It is thus difficult to accurately open and close the cups.

Further, there is a possibility that, when the insertion section of the treating instrument is to be inserted into a meandering duct or tract, an operation force involved upon the operation of the operation wire means will be partially absorbed, failing to accurately transmit such operation force to the distal end of the insertion section. It is thus difficult to accurately open and close the cups in a desired fashion.

SUMMARY OF THE INVENTION

It is accordingly the object of the present invention to provide a treating instrument which can make a drive mechanism of a treating unit on the distal-end side of an endoscope simple and compact and can narrow the diameter of the insertion sheath and also operate the treating unit accurately.

In order to achieve the object of the present invention, there is provided a treating instrument comprising an insertion section to be inserted into either one of a human body cavity for medical treatment and an industrial pipe and having a distal end and an operator-side end; a treating unit connected to the distal end of the insertion section; an operation member provided at the treating section to be movable between a standby position and an operative position so that a target region in a given cavity can be treated, an actuator mounted on the distal end of the insertion section and generating a drive force of the operation member; drive means for driving the actuator; grip means connected to the operator-side end of the insertion section; and means, provided on the grip means, for outputting a control signal for controlling an operation of the drive means.

According to the present invention, the treating unit can be driven by an actuator on the distal end of the insertion section, obviating the necessity of providing an operation wire means of a thickness enough great to transmit a drive mechanical operation force. As a result, the drive mechanism of the treating member on the distal end of the sheath can be made simple and compact and it is also possible to narrow the diameter of the insertion section and to accurately operate the treating unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3A is a longitudinal cross-sectional view showing a major portion of an operation means for driving a pair of cups and FIG. 3B is a longitudinal cross-sectional view showing a major portion of the pair of cups in an opened state;

FIG. 5A is a longitudinal cross-sectional view showing an intracavity stone crushing instrument according to a third embodiment of the present invention and FIG. 5B is a longitudinal cross-sectional view showing a variant of the third embodiment;

FIG. 13 is a perspective view showing a variant of the gripper;

FIG. 14A is a perspective view showing a storage state of basket wires at a basket type treating unit and FIG. 14B is a perspective view showing an extended state of basket wires;

FIG. 15A is a perspective view showing a storage state of a high-frequency surgical knife type treating unit and FIG. 15B is a perspective view showing an extended state of a high-frequency surgical knife type treating unit;

FIG. 16 is a diagrammatic view showing a degrees-of-multifreedom tubular manipulator according to a sixth embodiment of the present invention;

FIG. 20A is a diagrammatic view showing a microgripper according to a ninth embodiment of the present invention and FIG. 20B is a front view of the microgripper in FIG. 20A;

FIG. 21 is a diagrammatic view for explaining the operation of an actuator of FIG. 20B;

FIG. 25 is a perspective view showing a major section in a twelfth embodiment of the present invention;

FIG. 26 is a side view showing the major section in the embodiment of FIG. 25; and FIG. 27 is a perspective view showing a major section in a thirteenth embodiment of the present invention.

DETAILED DESCRIPTION OF THE PREFERRED EMBODIMENTS

Figure 1:
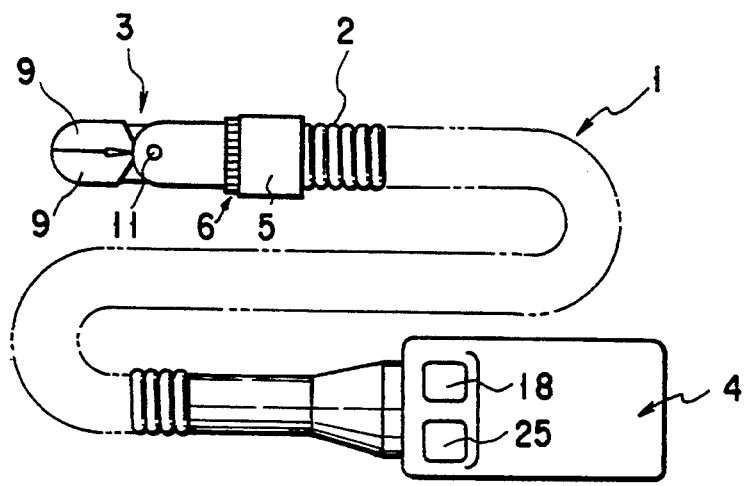
FIG. 1 is a side view generally showing biopsying forceps according to a first embodiment of the present invention.

FIGS. 1 to 4B show a first embodiment of the present invention. FIG. 1 shows biopsying forceps 1 as one form of a treating instrument for an endoscope. A flexible sheath 2 is provided on an insertion section of the biopsying forceps and comprised of a closely-turned coil.

A forceps (treating) unit 3 is provided at a distal end section of the sheath 2 and a grip means 4 is mounted on a base end of the sheath 2.

A distal tip section 5 of a bottomed-cylindrical configuration is provided on the forceps section 3. The bottom area of the distal tip section 5 is fixed to the distal-end side of the sheath 2.

Figure 2A:
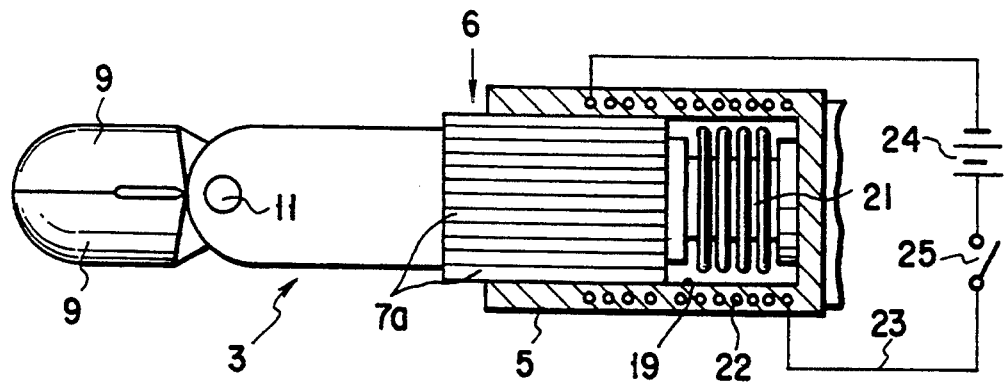
FIG. 2A is a longitudinal cross-sectional view showing a movable member of the forceps in FIG. 1

A movable member 6 is inserted in the cylinder of the distal tip section 5 and movable in an axial direction of the sheath 2. Splined grooves 7a are provided on the outer periphery of the movable member 6 and extend along the axial direction of the sheath 2 as shown in FIG. 2A.

Splined grooves are provided in the inner wall of the distal tip section to engage with the splined grooves 7a of the movable member 6. For this reason, the movable member 6 is held movable only in the axial direction of the sheath 2, not rotatable relative to the distal end section.

An operating means is provided at the movable member 6 as shown in FIG. 3A. The movable member 6 has a recess 7 at a base end portion and a slitted section 8 at a forward end portion.

A pair of cups 9, 9 are provided as an operation member with their bases 9a, 9a pivotally mounted by a pivotal pin 11 within the slitted section 8 of the forceps unit. A pair of links 12, 12 are connected at one end to the bases 9a, 9a of the cups 9, 9 and at the other end to the forward end of a rod-like metal drive member 13 serving as an actuator for opening and closing the cups. The pair of links 12, 12 are pivoted by a common pivotal pin 14 at those other ends of the respective links 12, 12. Thus a pantograph mechanism is provided by the bases 9a, 9a of the cups 9, 9 and links 12, 12 to enable the pair of cups 9, 9 to be opened or closed.

The drive member 13 is secured at the base end to the bottom wall of the recess 7 of the movable member 6. A heat generating coil 15 is turned around the outer periphery of the drive member 13 and connected to a power source 17, for example, in the grip means 4 through a lead wire 16 extending in the sheath 2. An operation switch 18 is provided in the grip means 4 to control the supply of electric current to the heat generation coil 15.

With the heat generating coil 15 in a non-conductive state, the drive member 13 is held in a normal state (a thermally not expanded state) where the cups 9, 9 are held in a closed state as shown in FIG. 3A.

With the heat generating coil 15 in a conductive state, the drive member 13 is thermally expanded by heat which originates from the heat generating coil 15. Through the thermal expansion of the drive member 13, the aforementioned pantograph mechanism is operated as shown in FIG. 3B to allow the pair of cups 9, 9 to be opened.

As a metal material for the drive member 13, various metals, such as, iron and copper, can be employed, but it is better to employ a material of high thermal expansion. It may be possible to employ a two-directional shape memory alloy.

In that recess 19 of the distal tip section 5 where the base portion of the movable member 6 is fitted, bellows 21 are located, as an actuator, relative to the base end of the movable member 6 as shown in FIG. 2A so that the bellows may be extended and contracted in the axial direction of the sheath 2 to enable the position of the cups to be moved. The bellows 21 are made up of a metal thin film and have an external diameter as small as, for example, about a few millimeters.

The forward end of the bellows 21 is secured to the base end of the movable member 6. The base end of the bellows 21 is fixed to the bottom wall of the recess 19 of the distal tip section 5. A low boiling point liquid, such as liquid paraffin or flon, is sealed in the bellows 21 in a hermetic fashion.

Further, the bellows 21 are formed using an electro-deposition plating method. That is, a mandrel is initially prepared from aluminum or plastics so as to conform to a configuration of bellows to be formed. Then a thin film, such as nickel, copper, gold or silver, is formed as a plated film on the outer surface of the mandrel and then the mandrel per se is dissolved, thus leaving the plated thin film as bellows. In this way, it is possible to form bellows set out above.

According to this method, the bellows can readily be made smaller in diameter and, for example, as thin as about a few tens of $\mu$m and as small as about 1 mm to a few millimeters in outer diameter.

A heat generating coil 22 is buried in the surrounding wall of the recess 19 of the distal tip section 5. It is to be noted that the heat generating coil 22 may be arranged on the inner wall surface of the recess of the distal tip section 5.

The heat generating coil 22 is connected to the power source 24 in the grip means 4 through the lead wire 23 extending in the sheath 2. An operation switch 25 is provided in the grip means 4 to control the supply of electric current to the heating coil 22.

The power sources 24 and 15 of the heat generating coils 22 and 17, respectively, are comprised of, for example, a battery unit, but an external power source may be used instead which is connected through a power source cord leading to the grip means 4 side.

Operating the biopsying forceps 1 will be explained in detail below.

The sheath 2, that is, the insertion section of the forceps 1, is inserted into a body cavity of a human subject through an insertion channel which has initially been inserted there and through which a treating instrument for an endoscope is inserted. At this time, the operation switches 18 and 25 are placed in a non-conductive state and hence no electric current is carried through the heat generating coils 15 and 22. That is, heat is not generated at the respective heat generating coils 15 and 22 and the forceps unit 3 are held in the states shown in FIGS. 2A and 3A where the cups 9, 9 are closed and hence the movable member 6 is contracted in the recess 19 of the distal tip section 5.

For the biopsy to be done in the body cavity of the human subject, the forceps unit 3 are advanced with the operation switch 25 of the grip means 4 ON and hence the heat generating coil 22 in the conductive state.

Figure 2B:
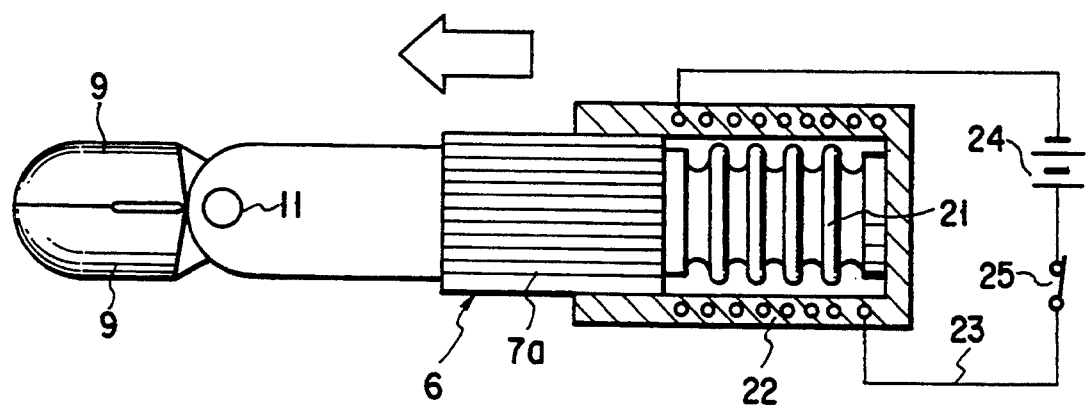
FIG. 2B is a longitudinal cross-sectional view showing the movable member in an advanced state.

The heat generating coil 22 is heated, expanding the liquid paraffin in the bellows 21 through vaporization and hence extending the bellows 21 in the axial direction. As a result, the cup-mount movable member 6 is pushed out and advanced as shown in FIG. 2B.

It is possible to adjust an amount of advance of the movable member 6 by controlling a power energy carried through the heat generating coil 22 and hence controlling the vaporization of the liquid paraffin and amount of expansion.

Opening and closing the cups 9, 9 will be explained below.

With the operation switch 18 of the grip means 4 ON, heat is generated at the heat generating coil 15 around the drive member 13. Upon the heat generation of the heat generating coil 15 and heating of the drive member 13 thereby, the drive member 13 is expanded in the axial direction as shown in FIG. 3B and the pair of cups 9, 9 are opened through the aforementioned pantograph mechanism.

With the operation switch 18 OFF, no electric current is carried through the heat generating coil 15 around the drive member 13, allowing the drive member 13 to be heat-dissipated and hence contracting the bellows back to its original position. Through this contraction action, the pair of cups 9, 9 are closed as shown in FIG. 3A.

Since the metal drive member 13 is provided on the distal end of the sheath 2 of the forceps 1 and the pair of cups 9, 9 of the forceps 1 are opened through the pantograph mechanism in accordance with the thermal expansion of the drive member 13, it is not necessary to provide an operation wire enough thick to transmit a mechanical operation force through the sheath 2. It is thus possible to narrow the diameter of the sheath 2, that is, the insertion section of the forceps 1, unlike the conventional counterpart.

Further, since the cups 9, 9 of the forceps 1 are opened or closed in accordance with the heat expansion of the metal drive member 13 on the distal end of the sheath 2, it is possible to more accurately open and close the forceps than in the conventional structure and to do so without the risk of an operation wife's drive force being partially absorbed partway upon the opening or closing of the pair of cups 9, 9 in the case where the sheath 2 of the forceps 1 is inserted in a meandering passage involved.

As the liquid paraffin-sealed bellows 21 are expanded due to the passage of electric current through the heat generating coil 22 in the distal tip section 5 and the vaporization of the liquid paraffin, that is, the movable member 6 is moved in the axial direction of the sheath 2, it is readily possible to perform the positional adjustment of the cups 9, 9 in the axial direction of the sheath.

Further, since the amount of advance of the movable member 6 can be adjusted by controlling an amount of electric energy passing through the heat generating coil 22 and hence the vaporization and expansion of the liquid paraffin, it can be accurately carried out as compared with the case where the amount of operation by the operation wire can be adjusted by a manual operation.

Figure 4A:
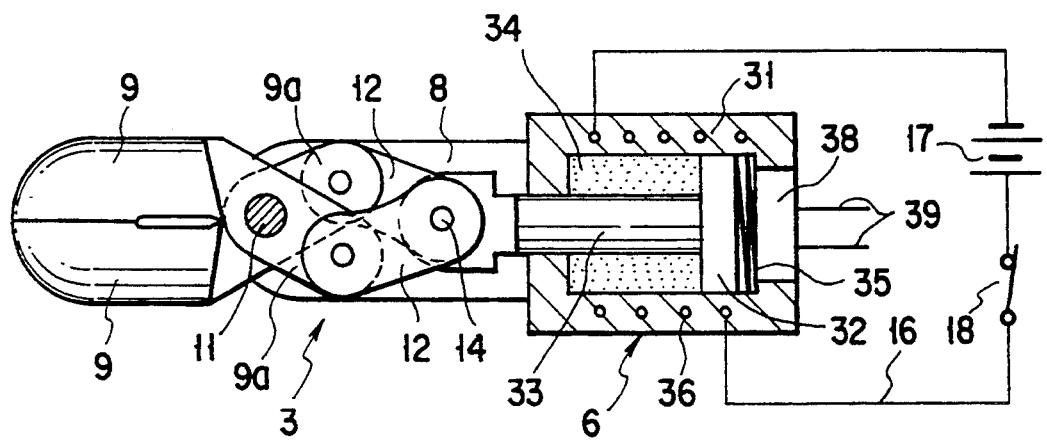
FIG. 4A is a longitudinal cross-sectional view showing a major portion of a forward end section of biopsying forceps according to a second embodiment of the present embodiment and FIG. 4B is a longitudinal cross-sectional view showing the major portion of a pair of cups in an opened state.
Figure 4B:
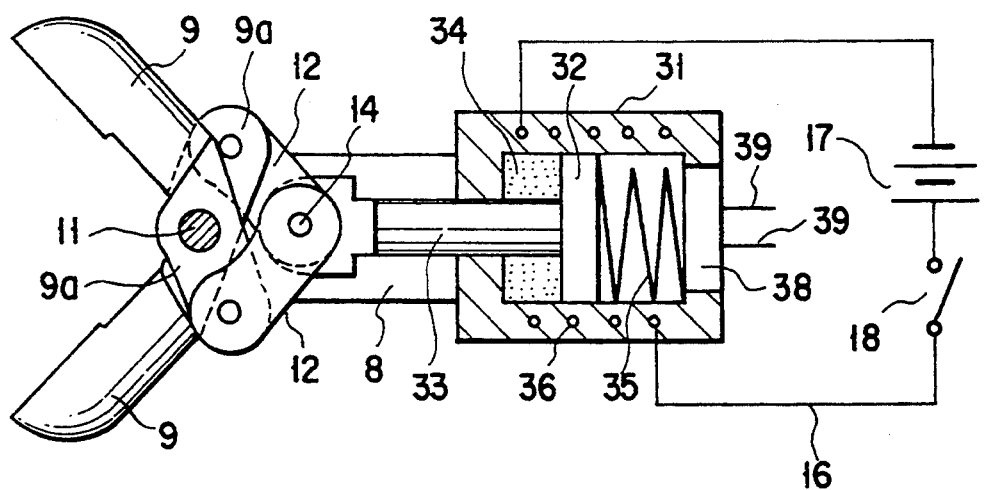

FIGS. 4A and 4B show a second embodiment of the present invention. This embodiment is different from the previous embodiment in that a different actuator is used in the biopsying forceps 1, that is, a cylinder 31 is provided relative to the base portion of a movable member 6 in the forceps unit 3 of the biopsying forceps 1.

A piston 32 is arranged in the cylinder 31 to be slidable in the axial direction of the cylinder. A piston rod 33 is connected at one end to the piston 32 and the other end of the piston rod hermetically extends past the forward end wall of the cylinder 31 into a slitted section 8 of the movable member 6. Links 12, 12 of a pantograph mechanism are pivoted by a common pin 14 on the extending end portion of the piston rod 33.

The cups 9, 9 are opened or closed when the piston 32 is moved in corresponding directions.

A low boiling point liquid 34, such as flon or liquid paraffin, is hermetically sealed in a front-side space of the cylinder 31 as defined by the piston 32. A coil spring 35 is provided in a back-side space of the cylinder 31 defined by the piston 32 such that it is urged in a forward direction.

A heat generating coil 36 is embedded in the peripheral wall of the cylinder 31 and connected to, for example, a power source 17 in the grip means 4 by a lead wire 16 which is arranged in the sheath 2. An operation switch 18 is provided in the grip means 4 to allow electric current to be carried through the heating means. The power source 17 is comprised of a battery unit, but may be an external power source connected to the grip means side through a power source cord.

A cooling means, such as a Peltier element 38, is located on the back wall side of the cylinder 31. The Peltier element 38 is employed upon the liquefaction of the liquid paraffin 34. When electric current is carried through the heat generating coil 36, the Peltier element 38 is not operated. The Peltier element 38 is connected to the operator-side control device via lead wires 39.

The operation of the forceps 1 will be explained below. Since the same operation as set out above in conjunction with the first embodiment is done except for the operation of cups 9, 9, explanation will be limited principally to opening and closing the cups 9, 9.

When the cups 9, 9 are to be closed, the operation switch 18 of the grip means 4 is turned ON as shown in FIG. 4A to allow electric current to be carried through the heat generating coil 36.

Heat is generated at the heat generating coil 36 to cause the liquid paraffin 34 in the front-side space in the cylinder 31 to be expanded through vaporization. The piston 32 is pushed backward by the expanded liquid paraffin against the urging force of the coil spring 35. Through the backward movement of the piston 32, the piston rod 33 is moved back to a right-side limit position in FIG. 4A, closing the cups 9, 9 through the pantagraph mechanism.

When the cups 9, 9 are to be opened, the operation switch 18 is turned OFF, causing the supply of the heat generating coil 36 to be stopped. By so doing, the liquid paraffin 34 in the forward-end space in the cylinder 31 emits heat spontaneously at which time the liquid paraffin 34 is liquefied more effectively through a cooling process when the Peltier element 38 is operated.

In this case, the volume of the liquid paraffin 34 is reduced and hence the piston 32 is advanced as shown in FIG. 4B under a combined force of a suction caused by the reduced volume of the liquid paraffin and an urging force of the coil spring 35.

Through the advance of the piston 32, the piston rod 33 is moved to a left-side limit position as shown in FIG. 4B, opening the cups 9, 9 through the pantograph mechanism.

By the movement of the piston 32 in the cylinder 31 provided on the distal end of the sheath 2 of the forceps 1 thus arranged, the cups 9, 9 are opened and closed, thus obtaining a diameter-reduced insertion section of the forceps 1 as in the case of the preceding embodiment and an accuracy with which the cups 9, 9 are operated.

FIG. 5A shows a third embodiment of the present invention. The third embodiment is employed as an intracavity stone-crushing instrument.

The base end of a bottomed-cylindrical connector 42 is connected to the distal end of a flexible sheath 41 which is comprised of an insertion section. An internally threaded section 42a is provided at the base end portion of the connector so that it can be threaded over an externally threaded section provided on the distal end portion of the flexible sheath 41. The connector 42 is detachably mounted on the distal end portion of the flexible sheath 41 through these internally and externally threaded sections.

A back-end section of a cylinder 43 is fitted over the forward end section of the connector 42. A reduced-diameter section 43a is provided, as an internal diameter section, on the forward-end side and an enlarged-diameter section 43b is provided, as an internal diameter section, on the back-end side of the cylinder 43. A piston 44 is disposed in the enlarged-diameter section 43b of the cylinder 43 such that it is slidably moved back and forth in the axial direction of the cylinder.

A treating rod 45 is provided on the front-end face of the piston 44 such that it can be extended outwardly or contracted inwardly via a forward open end 43c provided at the center face wall of the forward end portion of the cylinder 43.

A coil spring 47 is provided in the cylinder 43 such that it is wound around the outer periphery of the treating rod 45. One end of the coil spring 47 is inserted in the reduced-diameter section 43a of the cylinder 43 and the other end of the coil spring is stopped on the forward-end face of the piston 44. The piston 44 is pressed toward the connector 42 side by a spring force of the coil spring 47.

A liquid paraffin 34 of such a type as set out above is hermetically sealed in the base portion of the connector 42. Discharge electrodes 48a, 48b are provided at the base portion of the connector 42 to face the liquid paraffin 34 in the base portion of the connector 42.

Lead wires 49a, 49b connected to the corresponding discharge electrodes 48a, 48b lead to the operator's side through the flexible sheath 41 and to a power source unit 50. A switch 51 is provided in the power source unit 50 to supply voltage to the discharge electrodes 48a, 48b.

The operation of the stone-crushing instrument will be explained below.

Through an instrument insertion channel of the flexible sheath 41 of the endoscope, the stone-crushing instrument is inserted into a body cavity of a human being where a stone is formed. The forward end portion of the cylinder 43 is abutted against the stone in the body cavity of the human being.

The liquid paraffin 34 in the connector 42, being in a liquefied state, occupies a small volume and, therefore, the piston 44 is held to a right-side limit position where it abuts against an inner end of the connector 42 under an influence of the coil spring 47 as shown in FIG. 5A. At this time, the position of the forward end face of the treating rod 45 is held flush with the forward face of the cylinder 43.

By operating the operation switch 51 of the operator-side power source unit 50, a discharge occurs across the electrodes 48a and 48b, causing the liquid paraffin 34 to be instantly expanded. The piston 44 is advanced leftward (FIG. 5A) under an expansion pressure of the liquid paraffin 34 and the forward end of the treating rod 45 is extended out of the forward open end 43c of the cylinder 43 whereby a stone in the body cavity of the human being is crushed.

Thereafter the discharge is stopped and the liquid paraffin 34 is liquefied so that it is decreased in its volume. In this case, the piston 44 is returned, under the influence of the coil spring 47, back to an initial standby position.

In the arrangement shown, the piston 44 in the cylinder 43 which is provided on the distal end of the flexible sheath 41, that is, the insertion section of the stone-crushing instrument, is driven to enable the forward end of the treating rod 45 to be extended or contracted out of or into the cylinder 43. Since, in this case, the aforementioned specific arrangement, like the first embodiment, obviates the need to provide an operation wire, it is possible to narrow the diameter of the insertion section of the stone-crushing instrument and also to accurately operate the treating rod 45.

In the third embodiment shown, although the liquid paraffin 34 is heated by a discharge and hence expanded, it may be heated by a laser beam as shown in FIG. 5B.

In this embodiment, a laser guide fiber 61 is inserted through the flexible sheath 41 and the forward end of the laser guide fiber 61 faces an inner space in the connector 42 where a liquid paraffin 34 is hermetically sealed.

The base end of the laser guide fiber 61 is connected to a laser unit 62 on the operator's side. The laser unit 62 is connected to a controller 63 and an operation switch 64 is connected to the controller 63.

In the embodiment shown, a laser beam is directed at the liquid paraffin 34 through the laser guide fiber 61, heating the liquid paraffin. The other arrangement is the same as set out in conjunction with the aforementioned third embodiment.

Figure 6:
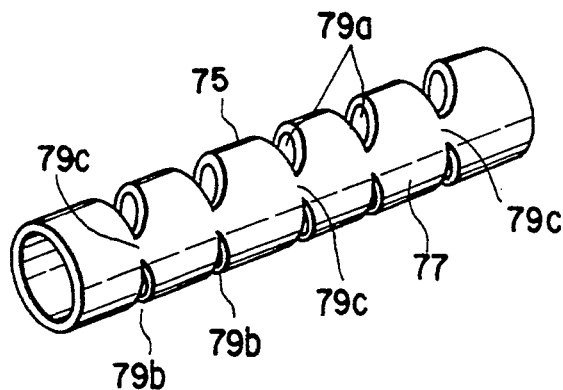
FIG. 6 is a perspective view showing a microarticulated unit.

The sheath 2 may be made up of a microarticulated unit 75 as shown in FIG. 6.

The microarticulated unit 75 includes two horizontal linear arrays of adjacent cutouts 79a, . . . and adjacent cutouts 79b, . . . in its thin-film tube 77 with a curvilinearly deformable hinge portion 79c provided between each cutout of one linear array and the corresponding adjacent cutout of the other linear array.

When the microarticulated unit 75 is curvilinearly deformed, the thin-film tube 77 as a whole is upwardly or downwardly curved with each hinge portion 79c as a bending point as viewed from an arrangement shown in FIG. 6.

The microarticulated unit 75 is manufactured in a way as set out below in conjunction with FIGS. 7A to 7D.

Figure 7A:
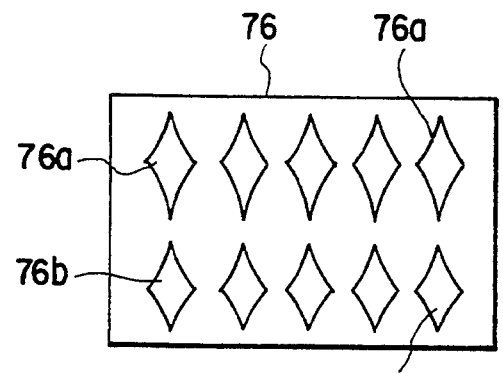
FIG. 7A is a plan view showing a mask for the macroarticulated unit.

A mask 76 of a desired pattern is manufactured as shown in FIG. 7A. Two horizontal linear arrays of cutouts 76a, . . . and 76b, . . . corresponding to cutouts 79a, . . . and 79b, . . . are provided in a pattern of a mask 76.

Figure 7B:
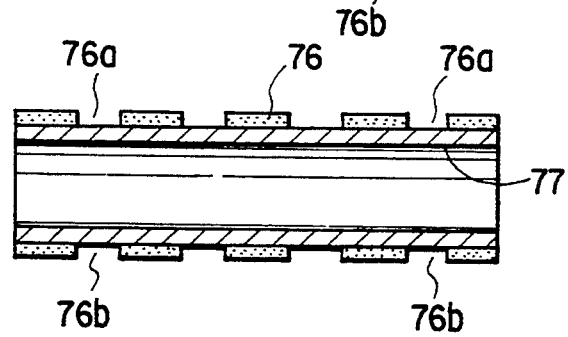
FIG. 7B is a longitudinal cross-sectional view showing the mask covered on the outer periphery of a thin-film tube.

As shown in FIGS. 7B, the mask pattern 76 is fitted over the outer periphery of a thin-film tube 77 whose diameter corresponds to the configuration of a product intended. In this way, a nonetched layer is provided.

Figure 7C:
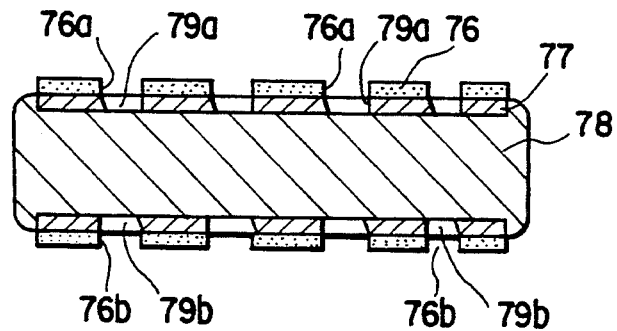
FIG. 7C is a longitudinal cross-sectional view for explaining an etched state of the thin-film tube and FIG. 7D is a longitudinal cross-sectional view showing a microarticulated unit.

A mandrel 78 as shown in FIG. 7C, serving as a nonetched layer, is inserted into the thin-film tube 77 and, in this state, etching is done on the resultant structure to provide cutouts 79a, . . . and 79b, . . . in the thin-film tube 77 as shown in FIG. 7C.

Figure 7D:
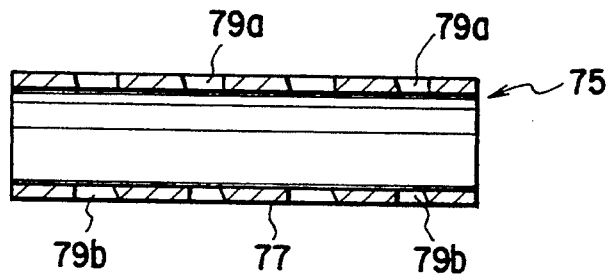

Then the mask 6 and mandrel 78 are removed off the thin-film tube 77 as shown in FIG. 7D to provide a desired microarticulated unit 75.

According to this method, it is possible to obtain a microarticulated unit 75 of below 0.1 mm in thickness and below 1 mm in outer diameter. By so doing, a microarticulated unit of a simple construction can be obtained without the need of assembling it.

Figure 8A:
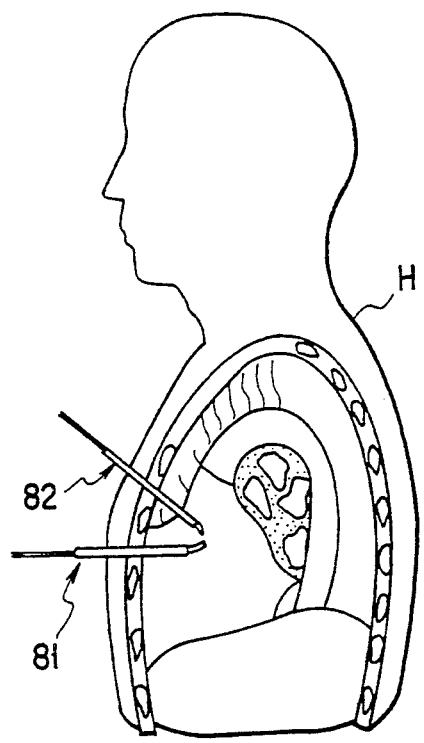
FIG. 8A is a diagrammatic view showing, in an operative state, a surgical operation microrobot according to a fourth embodiment of the present invention
Figure 9:
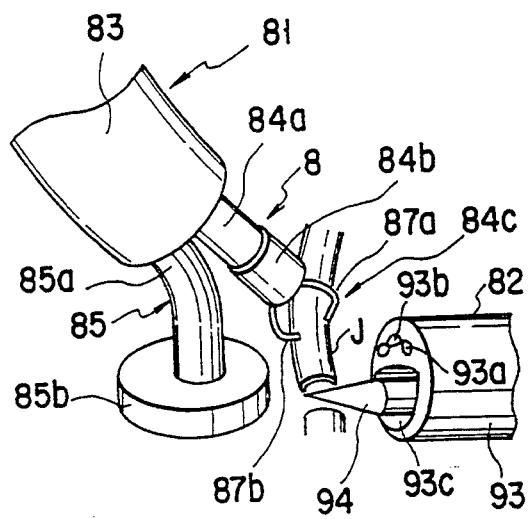
FIG. 9 is an expanded view diagrammatically showing a major portion of a microrobot for surgery.

FIGS. 8A to 10B show a fourth embodiment of the present invention. In FIG. 8A, reference numeral 81 shows a microrobot for use in surgically operating the coronary artery through a thoracic route in which case the microrobot serves as a treating instrument. 82 shows an endoscope provided separate from the microrobot 81. The microrobot 81 has an insertion section 83 of a multi-articulated structure which is flexibly bendable as shown in FIG. 8B. As shown in FIG. 9, one microgripper (treating unit) 84 and one fixed leg 85 are provided on the distal end of the insertion section 83 such that they are projected. The fixed leg 85 includes a fixed section 85b for suction to the forward end of a leg portion 85a. The fixed section 85b is fixed to a body cavity wall, etc., by a proper means, such as suction.

Figure 10A:
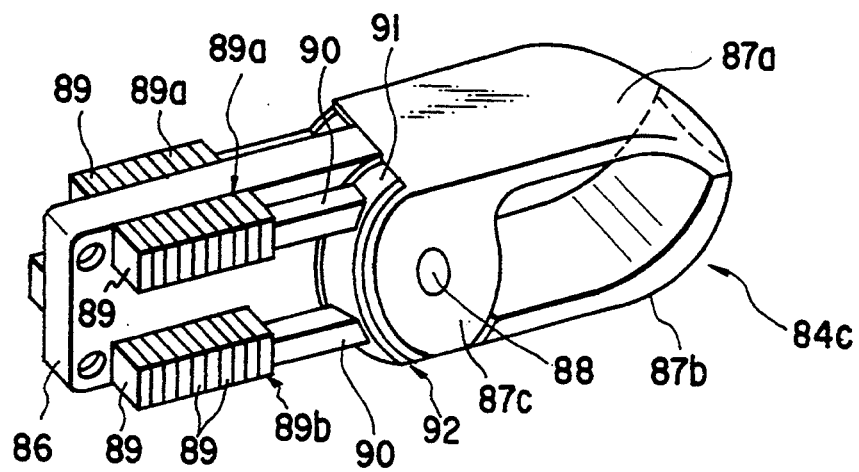
FIG. 10A is a perspective view showing a major portion of a gripper for a microrobot and FIG. 10B is a side view of the gripper.

The microgripper 84 includes a holder 84b fixed to the distal end of the flexible sheath 84a. A grip means 84c is held on the holder 84b and has a fixed frame 86 and a pair of sandwiching members (gripping arm) 87a, 87b, upper and lower, as shown in FIG. 10A.

A substantially circular coupling frame 87c is provided on the base portion of the upper-side sandwiching member 87a. The coupling frame 87c of the upper-side sandwiching member 87a is pivotally connected by a coupling pin 88 on the forward end portion of the fixed frame 86. The lower-side sandwiching member 87b is fixed to the forward end portion of the fixed frame 86.

A pair of piezoelectric element units 89a, 89b are provided on each side at the base end area of the fixed frame 86. The piezoelectric element units 89a, 89b are comprised of a plurality of stacked piezoelectric elements 89 which are displaced, upon conduction, in the thickness direction.

A rod-like contact member 90 is fixed to the forwardest piezoelectric element 89 and a friction plate 91 is fixed to the back end of the coupling frame 87c of the upper-side sandwiching member 87a. The contact members 90 of the piezoelectric element units 89a, 89b are disposed in an opposed relation to the friction plate 91.

A rotary type ultrasonic motor (actuator) 92 is comprised of the piezoelectric element units 89a, 89b and friction plate 91 of the sandwiching member 87a.

Upon conduction of one piezoelectric element unit 89a, the contact member 90 of the piezoelectric element unit 89a pushes against the friction plate 91, thereby closing the sandwiching member 87a. Upon conduction of the other piezoelectric element unit 89b, on the other hand, the contact member 90 of the piezoelectric element unit 89b pushes against the friction plate 91, thereby opening the sandwiching member 87a. Upon conduction of both the piezoelectric element units 89a, 89b, a braking action is applied, stopping the movement of the sandwiching member 87a.

The endoscope 82 has, like the microrobot 81, the insertion section 93 of a multi-articulated structure as shown in FIG. 9 which is flexibly bandable. An illumination window 93a of an illumination optical system, observation window 93b of an observation optical system, treating instrument insertion channel 93c, etc. are provided on the distal end portion of the insertion section 93. A treating instrument 94 for resection is inserted into the instrument insertion channel 93c to enable a blood vessel region of interest to be resected.

The operation of the microrobot 81 for surgical operation will be explained below.

In the case where, for example, the coronary artery is clogged during a treatment on the myocardial infraction, the microrobot can perform a bypass operation by resecting the clogged area of the coronary artery and joining together those remaining areas of the artery.

During such a treatment, the insertion section 83 of the microrobot 81 and insertion section 93 of the endoscope 82 are independently inserted into the thorax of a patient H through the outer skin as shown in FIG. 8A.

Figure 8B:
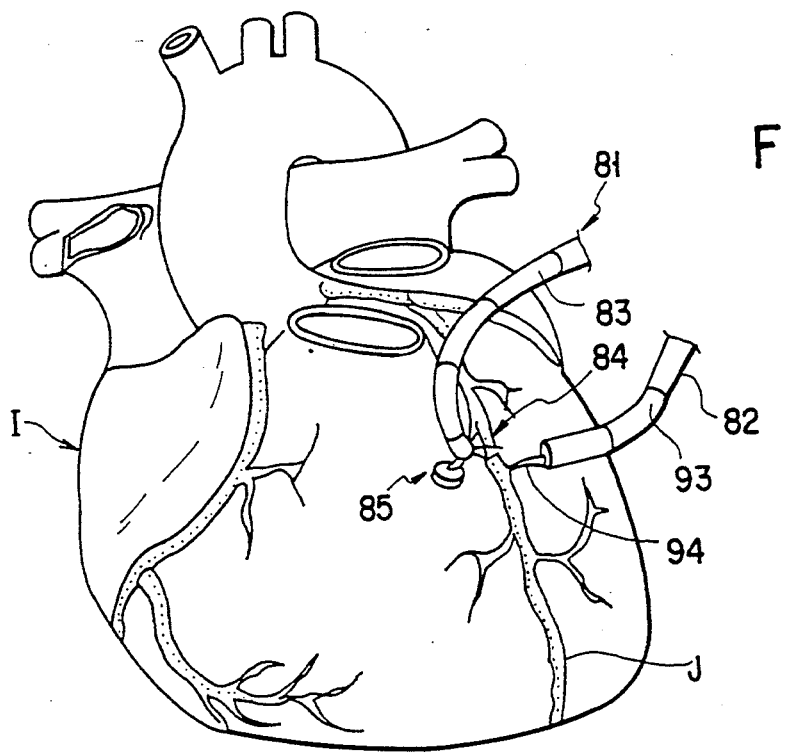
FIG. 8B is a diagrammatic view showing a state in which a bypass operation is done in the coronary artery of the heart.

The forward end of the insertion section 83 of the microrobot 81 is guided into a target region of the patient while observing the body cavity through the endoscope 82. Since, in this case, the insertion sections 83 and 93 of the microrobot 81 and endoscope 82, respectively, are flexibly bent due to their multiarticulated structure, it can also be positively guided into a back side of the heart I of the patient H as shown in FIG. 8B.

After the forward end of the microrobot 81 has been guided onto the target region of the body cavity, the microrobot 81 is set by the fixed leg 85 in the neighborhood of the target region in the body cavity of the patient.

Then as shown in FIG. 9, the bypass operation of the coronary artery J is carried out by the microgripper 84 of the microrobot 81 and resecting instrument 94 inserted through the insertion channel 93 of the endoscope 82.

During the operation by the microrobot gripper 84 of the microrobot 81, the upper-side sandwiching member 87a is opened or closed by the rotary type ultrasonic motor 92. The sandwiching member 87a is opened as indicated by a phantom line in FIG. 10B by pushing the contact member 90 of the piezoelectric element unit 89b against the friction plate 91 by the conduction of the piezoelectric element unit 89b.

Further, the sandwiching member 87a is closed by pushing the contact member 90 of the piezoelectric element unit 89a against the friction plate 91 by the conduction of the piezoelectric element unit 89a. Braking is applied when both the piezoelectric element units 89a and 89b are turned ON. In this way, the sandwiching member 87a is stopped.

In the aforementioned arrangement, the sandwiching member 87a of the grip means 84c is opened and closed by the rotary type ultrasonic motor 92 provided on the forward end of the microrobot 81. This embodiment, like the first embodiment, can narrow the diameter of the insertion section 83 of the microrobot 81 as compared with the case where the sandwiching member 87a of the grip means 84c is opened and closed by the operation wire. It is possible to accurately operate the grip means 84c.

Figure 11A:
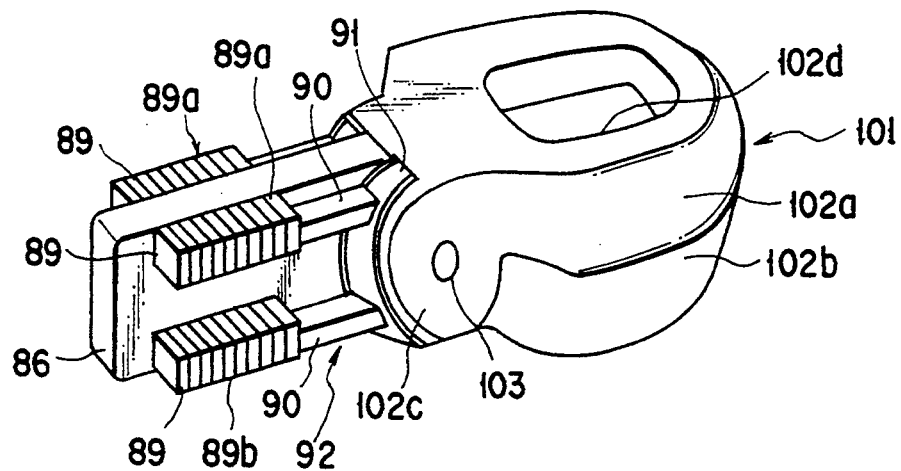
FIG. 11A is a perspective view showing a biopsying forceps type treating unit for a microrobot and FIG. 11B is a perspective view showing a scissor forceps type treating unit.
Figure 11B:
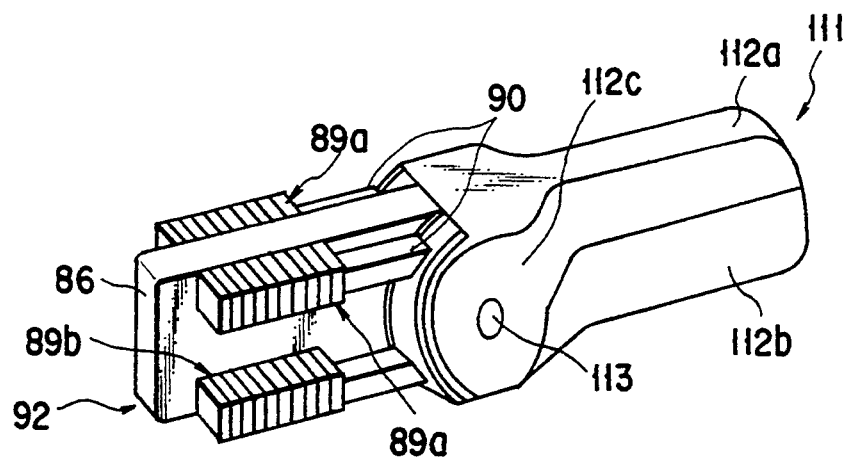

Although, in the aforementioned embodiment, the grip means 84c equipped with the pair of sandwiching members 87a, 87b has been explained as being the treating instrument of the microrobot 81, it is also possible to employ a biopsying forceps type treating instrument 101 as shown in FIG. 11A or a scissor forceps type treating instrument 111 as shown in FIG. 11B.

The treating instrument 101 as shown in FIG. 11A has a pair of openable/closable cups 102a, 102b each with a hole 102d formed therein. Further, a coupling frame 102c of a substantially circular configuration is mounted on the base end portion of the cup 102a.

The coupling frame 102c of the cup 102a is rotatably connected by a coupling pin 103 to the forward end of a fixed frame 86. The cup 102a of the treating unit 101 can be opened or closed by a rotary type ultrasonic motor 92 mounted on the forward end of the microrobot 81.

The treating instrument 111 as shown in FIG. 11B has a pair of openable/closable cutting edges 112a, 112b. A substantially circular coupling frame 112c is provided on the base end portion of the cutting edge 112a. The coupling frame 112c of the cutting edge 112a is rotatably connected by a coupling pin 113 to the forward end of the fixed frame 86. The cutting edge 112a of the treating instrument 111 can be opened and closed by a rotary type ultrasonic motor 92 mounted on the forward end of the microrobot 81.

Figure 12C:
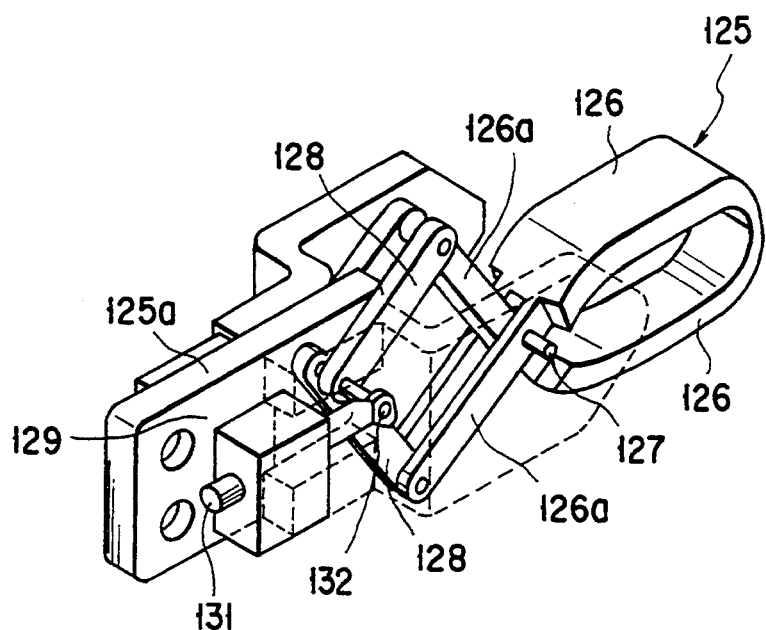
FIG. 12C is a perspective view showing a microgripper and FIG. 12D is a diagrammatic view showing a linear type ultrasonic motor.
Figure 12D:
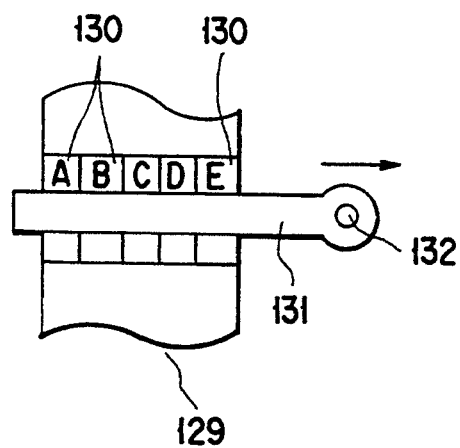
Figure 12A:
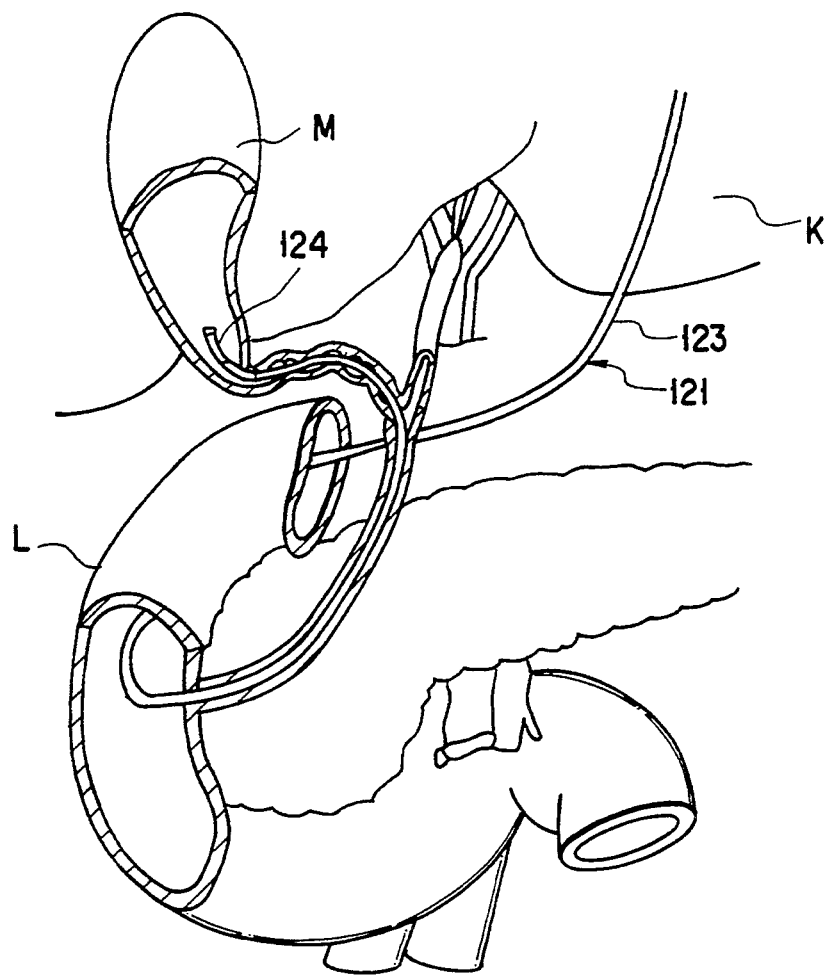
FIG. 12A is a diagrammatic view showing, in an operative state, a treating instrument according to a fifth embodiment of the present invention.
Figure 12B:
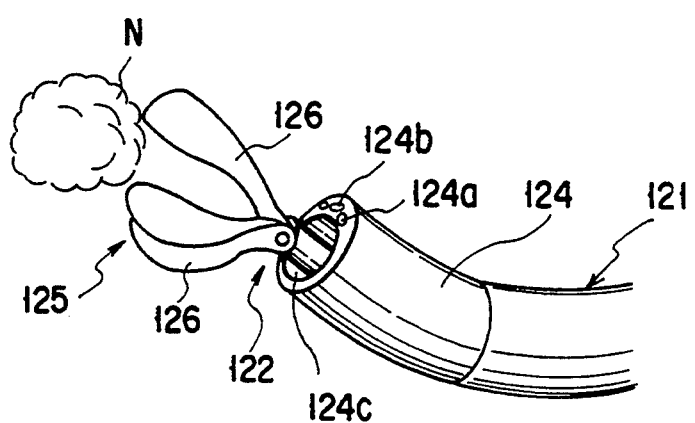
FIG. 12B is a perspective view showing a state in which a microgripper is projected out of an insertion channel of a treating instrument for an endoscope.

FIGS. 12A to 12D show a fifth embodiment of the present invention. This embodiment is applied to a treating instrument 122 which is inserted into a body cavity of a human being, as shown in FIG. 12A, through an endoscope 121 shown in FIG. 12B.

The endoscope 121 has a flexible, but soft, insertion unit 123. A forward-end structural unit 124 is connected through a curved section to a distal-end side of the insertion section 123.

The forward-end structural unit 124 has, on the forward end face side, an illumination window 124a for an illumination optical system, observation window 124b of an observation optical system, instrument insertion channel 124c, etc. The treating instrument 122 is inserted through the insertion channel 124c.

A linear type ultrasonic drive microgripper 125 as shown in FIG. 12c is mounted on the insertion section of the treating instrument 122, for example, on the distal end of a flexible sheath comprised of, for example, a tightly wound coil. A fixed frame 125a and pair of sandwiching members (treating unit) 126,126 are provided on the microgripper 125.

The sandwiching members 126,126 are mounted by a coupling pin 127 on the fixed frame 125a so that they are opened and closed relative to each other. Links 128, 128 are connected at one end to base-end coupling arms 126a of the respective sandwiching members 126 and 126. The other end of each link (128, 128) is pivoted by a pivotal pin 132 to the forward end of an operation shaft 131 of a linear type ultrasonic motor 129. The motor 129 is comprised of an actuator for opening/closing drive.

A casing of the linear type ultrasonic motor 129 is secured to a fixed frame 125a. The links 128, 128 and coupling arms 126a, 126a of the sandwiching members 126. 126 provide a pantagraph mechanism for opening and closing the sandwiching members 126,126.

A plurality of piezoelectric elements 130, . . . are arranged in a parallel array around the operation shaft 131 in the linear type ultrasonic motor 129 as shown in FIG. 12D. At the operation time of the linear type ultrasonic motor 129, a travelling wave is generated by the piezoelectric elements 130, . . . and the operation shaft 131 is operatively moved in the direction of the travelling wave whereby the sandwiching members 126,126 in the microgripper 125 are opened and closed through the action of the pantagraph mechanism.

The function of the aforementioned treating instrument 122 will be explained below.

The treating instrument 122 for the endoscope is guided onto a region of interest of the patient through the instrument insertion channel 124c of the endoscope 121 which has been inserted through the mouth into a given region of the body cavity. For example, as shown in FIG. 12A, the endoscope 121 is orally guided into the gallbladder M through a route L of the oesophagus, stomach, duodenum, etc. and the treating instrument 122 is inserted through the insertion channel 124c of the endoscope 121 into the gallbladder M.

A stone N in the gallbladder M is crushed by the opening/closing operation of the microgripper 125 of the treating instrument 122. At the opening/closing operation of the microgripper 125, the linear type ultrasonic motor 129 is driven so that the operation shaft 131 is operatively moved. The operation shaft 131 is moved in a direction to push the coupling pin 127 toward the forward-end side as indicated by an arrow in FIG. 12D. By so doing, the sandwiching members 126, 126 in the microgripper 125 are opened through the action of the pantagraph mechanism.

By moving the operation shaft 131 in a direction to pull the coupling pin 127 toward the operator's side, the sandwiching members 126,126 of the microgripper 125 are closed through the operation of the pantagraph mechanism.

In the aforementioned arrangement, the sandwiching members 126,126 in the microgripper 125 are opened/closed by the linear type ultrasonic motor 129 provided on the forward end of the treating instrument 122. The embodiment as set out above, like the first embodiment, can narrow the diameter of the insertion section of the treating instrument 122 as compared with the case where the sandwiching members 126,126 in the microgripper 125 are opened and closed through an operation wire. It is possible to accurately operate the microgripper 125.

FIG. 13 shows a variant of the treating unit mounted on the forward end of the treating instrument 122. In this variant, a substantially L-bent section 142 is provided on a fixed frame 141 of the linear type ultrasonic motor 129 and a circular hole 142a is provided in the L-bent section 142.

A gripper 143 is mounted on an operation shaft 131 of a linear type ultrasonic motor 129 and has three hook projections 143a, ... made of a superelastic alloy material. The three hook projections 143a, ... of the gripper 143 extend out of the circular hole 142a of the fixed frame 141. By the pull of the operation shaft 131 by the linear type ultrasonic motor 129, the hook projections 143a, ... of the gripper 143 are withdrawn through the circular hole 142a of the fixed frame 141 and closed. By pushing the operation shaft 131 by the ultrasonic motor 129, the three hook projections 143a, of the gripper 143 are pushed out through the circular hole 142a and spread open.

FIGS. 14A and 14B show another variant.

In this variant, a cylindrical storage section 151 is provided between a linear type ultrasonic motor 129 and a bent section 142 of a fixed frame 141 of the motor and a basket type treating unit 152 is mounted on an operation shaft 131 of the ultrasonic motor and has a plurality of basket wires 152a, ... which can be opened and closed.

The basket wires 152a, ... of the basket type treating unit 152 are inserted into the storage section 151 of the fixed frame 141. By withdrawing the operation shaft 131 by the ultrasonic motor 129, the basket wires 152a, ... are pulled back in the storage section 151 of the fixed frame 141 as shown in FIG. 14A.

By extending the operation shaft 131 by the ultrasonic motor 129 in a forward direction, the basket wires 152a, ... are pushed out of the storage section 151 of the fixed frame 141 as shown in FIG. 14B and spread open.

FIGS. 15A and 15B show another variant. In this variant, a high-frequency surgical knife type treating unit 161 is provided instead of the basket type treating unit 152.

By withdrawing an operation shaft 131 by a linear type ultrasonic motor 129, the high-frequency surgical knife type treating unit 161 is pulled back into a storage section 151 of a fixed frame 141 and closed as shown in FIG. 15A. By extending the operation shaft 131 by the linear type ultrasonic motor 129, the high-frequency surgical type treating unit 161 is pushed out of a storage section 151 of the fixed frame 141 and exposed as shown in FIG. 15B.

FIG. 16 shows a sixth embodiment of the present invention. This embodiment is applied to a treating unit for an industrial endoscope 171 which is inserted into the industrial pipe or duct, such as a gas pipe.

An illumination device 172 and pair of CCD cameras 173, 173 for observation are mounted on the distal end section of the industrial endoscope 171. Three short-length tubular manipulators 174a, 174b, 174c for the work in the pipe are fixed at the base end and has the degrees of multi-freedom. The manipulators 174a, 174b, 174c are of a flexibly bendable multiarticulated structure.

An illumination device and observation means, such as CCD cameras, are mounted on the forward end portion of the first manipulator 174a. A work area-enlargeable endoscopic system unit is provided which can monitor a repair spot Q, by the first manipulator 174a, in the industrial pipe P in close proximity in a direct-viewing fashion.

Figure 10B:
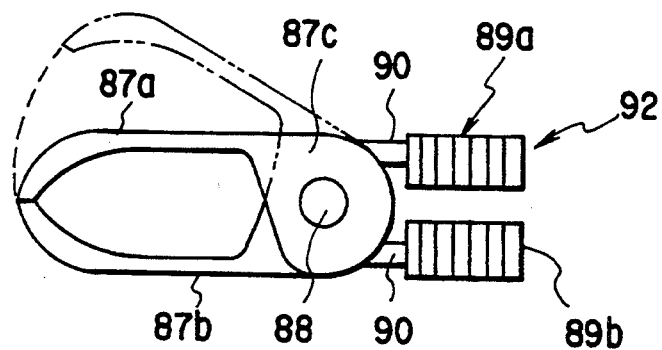

A microgripper 175 made up of grip means as shown, for example, in FIGS. 10A and 10B is mounted on the forward end of the second manipulator 174b. A tool conveying section is also provided which, while gripping a working tool, such as welding parts 176, by the microgripper 175, can be brought to the neighborhood of the repair spot Q.

An exit section for a laser beam, etc., as well as a grinder work unit, such as a grinder, is mounted on the forward end of the third manipulator 174c. That is, a work unit is provided so that, by the third manipulator 174c, welding is effected at and in close proximity to the repair spot Q in the industrial pipe and that grinding is effected by means of a grinder for repair.

In the arrangement above, the microgripper 175 comprised of the grip means as shown in FIGS. 10A and 10B is mounted on the forward end of the second manipulator 174b and the sandwiching member 87a can be opened and closed by a rotary type ultrasonic motor 92. For this reason, the embodiment above can narrow the diameter of the second manipulator 174b as in the case of the first embodiment and enables the basket type treating unit 152 to be operated accurately.

The microgripper of the fourth embodiment may be modified in the following way.

FIGS. 17A to 17D show a seventh embodiment of the present invention.

A treating unit 185 comprised of a fixed gripping section 182 and movable gripping section 184 is mounted in a microgripper 181. The movable gripping section 184 is mounted on the fixed gripping section 182 such that it is rotatable around a rotation shaft 183. A substantially circular coupling frame 184a is provided on the base end of the movable gripping section 184 such that it is rotatable by the rotation shaft 183 on the base end portion of the fixed gripping section 182.

Figure 17A:
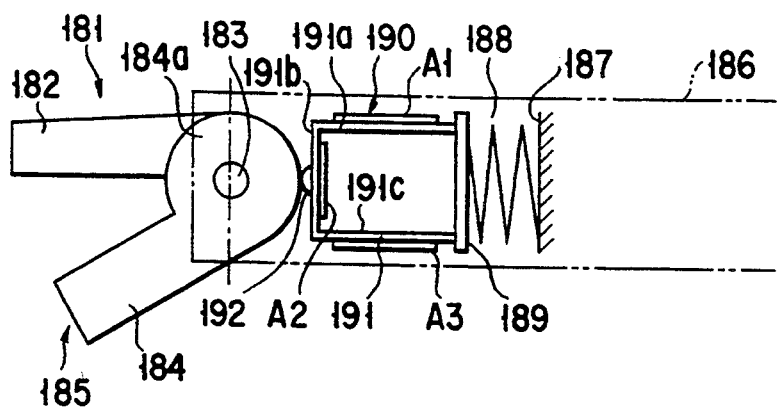
FIG. 17A is a diagrammatic view showing a microgripper according to a seventh embodiment of the present invention.
Figure 17B:
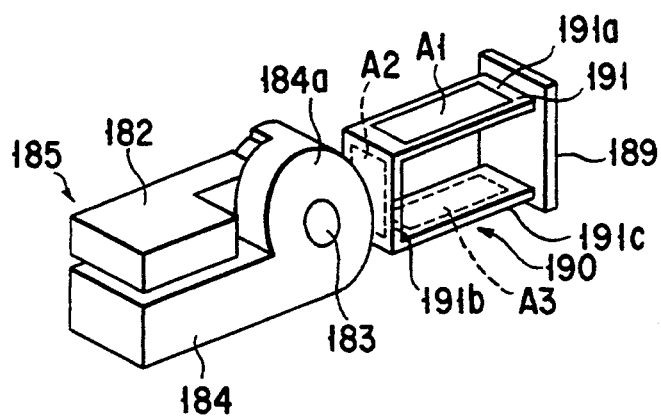
FIG. 17B is a perspective view of the microgripper.
Figure 17C:
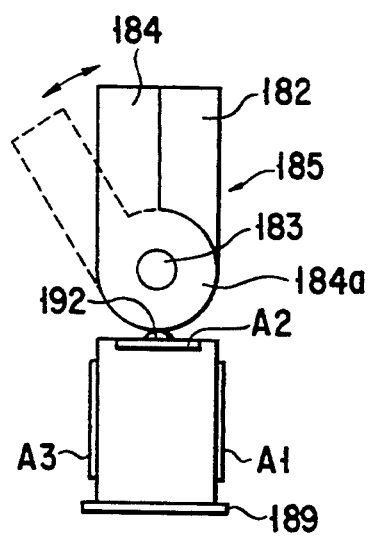
FIG. 17C is a front view of the microgripper and FIG. 17D is a diagrammatic view for explaining the operation of an actuator in the microgripper of FIG. 17A.

In FIG. 17A, reference numeral 186 shows a flexibly bendable multiarticulated manupulator. An actuator fixing plate 189 is mounted, through a spring means 188, relative to a fixed section 187 on the distal end of the manupulator 186.

The actuator 190 is mounted on a fixed plate 189 so as to open and close the movable gripping section 184 of the microgripper 181. An elastic plate 191 bent nearly like a channel is provided on the actuator 190.

The elastic plate 191 has a middle fixed portion 191b and opposed side portions 191a and 191c provided on both the sides of the middle portion 191b, noting that these opposed side portions are bent in a backward direction with their free ends fixed to the actuator fixing plate 189.

Piezoelectric elements A1 and A3, such as PZT, are fixed to the outer surfaces of the opposed side portions 191a and 191c. A contact member 192 is mounted on the outer surface of the fixed portion 191b of the elastic plate 191 and a piezoelectric element A2, such as PZT, is mounted on the inner surface of the fixed portion 191b of the elastic plate 191. The piezoelectric elements A1 and A3 are contracted when a voltage is applied and the piezoelectric element A2 is expanded when a voltage is applied.

The actuator 190 is of such a type that the contact member 192 of the elastic plate 191 is normally held, by a spring force of the spring member 188, in pressure contact with the coupling frame 184a of the movable gripping section 184.

At the operation time of the actuator 190, the three piezoelectric elements A1, A2 and A3 take the following four states: a first state of A1, A2 and A3 held without the application of voltage, a second state of A3 held with a voltage applied thereto, a third state of A2 held with a voltage applied thereto and a fourth state of A1 held with a voltage applied thereto. In this case, a sequential switching is carried out in this order of the four states.

Figure 17D:
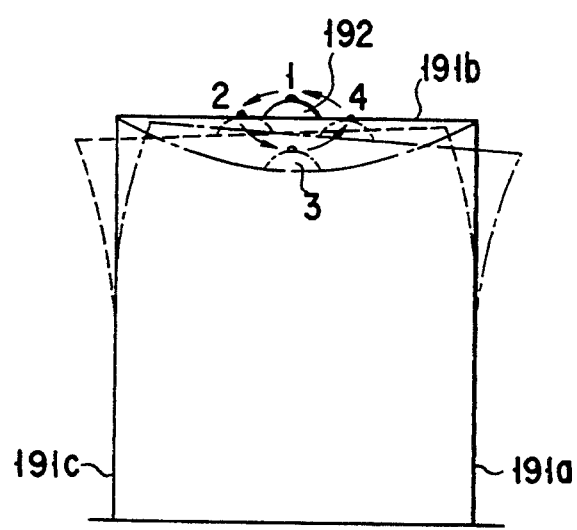

In the first state, the elastic plate 191 is held normally in a non-deformed state as indicated by a solid line in FIG. 17D. In this state, the contact member 192 of the elastic plate 191 is held normally in a position, as indicated by 1 in FIG. 17D.

In the second state, the piezoelectric element A3 is contracted. The side portion 191c of the elastic plate 191 is bent to the left, as indicated by a dotted line in FIG. 17D, due to the contraction of the piezoelectric element A3. In this state, the contact member 192 is operatively mounted up to a position, as indicated by 2 in FIG. 17D, due to the deformation of the whole elastic plate 191.

In the third state, the piezoelectric element A2 is expanded and, due to an expansion motion of the piezoelectric element A2, the fixed portion 191b of the elastic plate 191 is bent downwardly as indicated by a double-dot dash line in FIG. 17D. In this state, the contact member 192 is operatively moved up to a position, as indicated by 3 in FIG. 17D, due to the whole deformation motion of the elastic plate 191.

In the fourth state, the piezoelectric element A1 is contracted and, due to the contraction motion of the piezoelectric element A1, the side portion 191a of the elastic plate 191 is bent to the right as indicated by a single-dot dash line in FIG. 17D. In this state, due to the deformation motion of the elastic plate 191, the contact member 192 is operatively moved up to a position, as indicated by 4 in FIG. 17D.

Through the repetitive operations of the three piezoelectric elements A1, A2 and A3 in the aforementioned order, the contact member 192 is moved along a substantially elliptic locus. By the rotation of the contact member 192 along such an elliptic locus it is possible to operatively move the movable gripping section 184 in a direction to be opened.

By sequentially switching the voltage application order of the piezoelectric elements A1, A2 and A3 in a reverse sequence, it is possible to operatively move the movable gripping section 184 in a direction to be closed.

Since, even in this arrangement, the movable gripping section 184 of the microgripper 181 is moved by the actuator 190 at the distal end of the insertion section 83 in a direction to be opened and closed, the insertion section of the treating unit can be made narrower in diameter as in the case of the first embodiment than in the case where such a movable gripping section 184 of the microgripper 181 is opened and closed by the operation wire. It is also possible to more accurately operate the microgripper 181.

Figure 18:
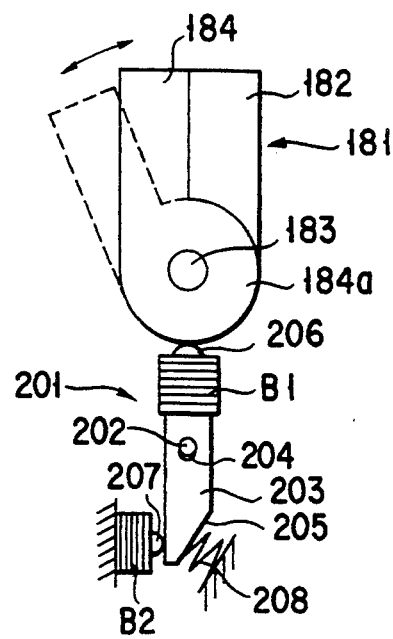
FIG. 18 is a diagrammatic view showing a major part of an eighth embodiment of the present invention.
Figure 19:
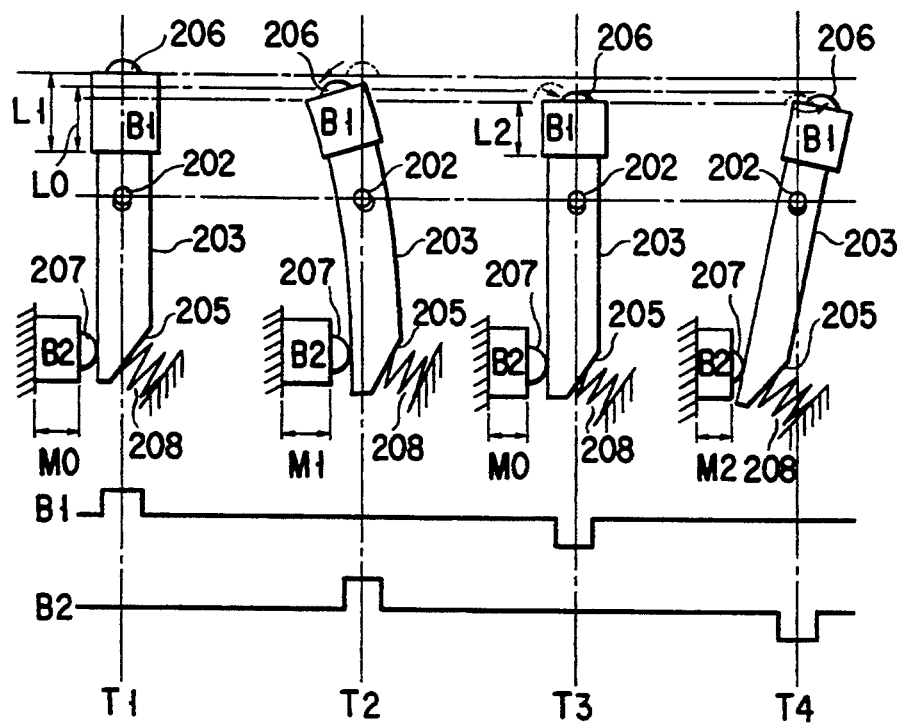
FIG. 19 is a diagrammatic view for explaining the operation of an actuator in the eighth embodiment.

FIGS. 18 and 19 show an eighth embodiment of the present invention. This embodiment constitutes a variant of the seventh embodiment of the present invention.

An operation rod 203 is provided on an actuator 201 of this embodiment and is so connected as to be rotatable around a support shaft 202 on a fixed section 187 side. An elongated hole 204 is formed in the operation rod 203 in an axial direction with the support shaft 202 provided in the elongated hole 204.

An obliquely cut surface 205 is formed, in an axial direction of the operation rod 203, on the outer periphery of the base end side of the operation rod 203. A spring means 208 on the fixed section 187 side is abutted against the obliquely cut surface 205 of the operation rod 203.

A stacked type piezoelectric element unit B2 is provided on the outer periphery of the base end side of the operation rod 203 such that it is located on a side opposite to that on which the obliquely cut surface is provided. A contact member 207 is fixed to the forward end of the stacked type piezoelectric element unit B2.

A stacked type piezoelectric element unit B1 is provided on the forward end side of the operation rod 203 with a contact member 206 fixed to the forward end of a stacked type piezoelectric element unit B1. The operation rod 203 is normally held, by the spring means 208, in pressure contact with a coupling frame 184a of a movable gripping section 184 and the contact member 207 is normally held in pressure contact with the outer periphery of the base end side of the operation rod 203.

With a supply voltage set at a constant reference voltage, the lengths of the piezoelectric element units B1 and B2 are held to constant dimensions L0 and M0, respectively. The stacked type piezoelectric element units B1 and B2 are expanded from their reference dimensions L0 and M0 to those dimensions L1 and M1 when the supply voltage is higher than a reference voltage and contracted from the reference dimensions L2 and M2 to smaller dimensions L2 and M2 when a voltage is supplied at a level smaller than the reference voltage.

At the operation time of the actuator 201, the stacked type piezoelectric element units B1 and B2 are moved in a sequential operation order to those positions T1→T2→T3→T4.

By the repeated expansion and contraction of the two stacked type piezoelectric element units B1 and B2 in the actuator 201, the contact member 206 is moved along a substantially elliptic locus, enabling the movable gripping section 184 of the microgripper 181 in a direction to be opened and closed. It is thus possible to narrow the diameter of the insertion section of the treating unit as in the case of the first embodiment when being compared with the case where the movable gripping section 184 of the microgripper 181 is opened and closed through the operation of the operation wire. It is also possible to more accurately operate the microgripper 181.

FIGS. 20A, 20B and 21 show a ninth embodiment of the present invention. This embodiment constitutes a variant of the actuator of a microgripper 181 of the present invention.

An elastic plate 212 is provided in an actuator 211 of the embodiment with the base end side of the elastic plate 212 mounted, by a spring means 214, relative to a fixed section 187 side.

A stacked type piezoelectric element unit C is mounted on the forward end side of the elastic plate 212 with a contact member 213 fixed on the forward end of the piezoelectric element unit C.

A pair of single layer type piezoelectric elements D, E are provided one on one side and one on the other side of the elastic plate 212. An actuator 211 is of such a type that the contact member 213 is normally held, by the spring means 214, in pressure contact with a coupling frame 184a of a movable gripping section 184.

With a supply voltage held at a constant reference level, the length of the stacked type piezoelectric element unit C is held to a reference dimension N0. The piezoelectric element unit C is expanded to a longer dimension N1 when a voltage is supplied at a level higher than the reference voltage and contracted from the reference dimension N0 to a shorter dimension N2 when a voltage is supplied at a level lower than the reference voltage.

In the case where the single layer type piezoelectric elements D and E are held to a reference dimension when the supply voltage is applied to the piezoelectric elements D and E and are expanded to a greater length when a voltage is supplied at a level higher than a reference voltage and contacted to a smaller length when a voltage is supplied at a level lower than the reference voltage.

At the operation time of the actuator 211, the piezoelectric element unit C and piezoelectric elements D and E are moved, in a sequentially repeated order, to those positions T1→T2→T3→T4.

Even in this case, the piezoelectric element unit C and piezoelectric elements D and E in the actuator 211, upon being expanded and contracted in a repeated way, enable the contact member 213 to be rotated along a substantially elliptic locus. By the rotation of the contact member 213 in elliptic motion, the movable gripping section 184 of the microgripper 181 can be opened and closed. In this embodiment, it is possible to narrow the diameter of the insertion section of the treating unit as in the case of the first embodiment when being compared with the case where the movable gripping section 184 of the microgripper 181 is opened and closed by the operation wire. It is also possible to more accurately operate the microgripper 181.

Figure 22:
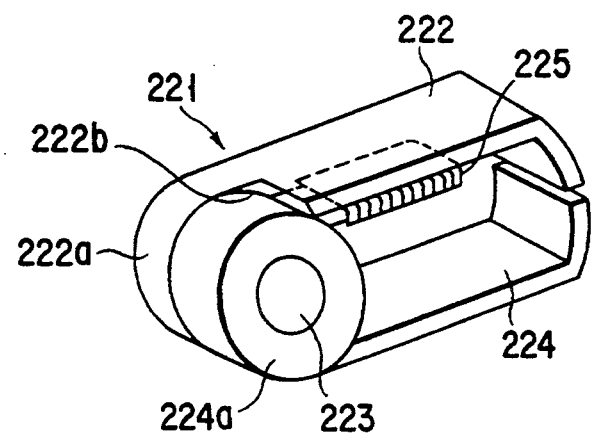
FIG. 22 is a perspective view showing a major part in a tenth embodiment of the present invention.

FIG. 22 shows a tenth embodiment of the present invention. In this embodiment, a microgripper 221 has a fixed gripping section 222 and movable gripping section 224. The movable gripping section 224 is connected to the fixed gripping section 222 such that it is rotatable around a rotation shaft 223.

Substantially circular coupling frames 222a and 224a are provided at those base ends of the fixed and movable gripping section 222 and 224, respectively. The coupling frame 224a of the movable gripping section 224 is rotatably coupled by the rotation shaft 223 to the coupling frame 222a of the fixed gripping section 222.

A spring means, not shown, is provided on the rotation shaft 223 to allow the forward end portion of the movable gripping section 224 to be urged in a direction to be opened relative to the fixed gripping section 222. The forward end portion of the movable gripping section 224 is normally held, by that spring means, in an opened state.

A cutout 222b is provided on the base end portion of the fixed gripping section 222 so as to prevent an interference with the coupling frame 224a of the movable gripping section 224. A stack type piezoelectric element unit (actuator) 225 is provided on the inner surface of the fixed gripping section 222 at an area near the cutout 222b. The forward end of the stacked type piezoelectric element unit 225 abuts against the coupling frame 224a of the movable gripping section 224.

At the operation time of the microgripper 221, the piezoelectric element unit 225 is deformed (expanded/contracted) so that the coupling frame 224a of the movable gripping section 224 is hit by the forward end of the piezoelectric element unit 225 to enable the forward end of the movable gripping section 224 to be moved in a direction to be closed relative to the fixed gripping section 222 against an action of the spring. By so doing, a target is gripped between the movable gripping section 224 and the fixed gripping section 222.

Since, even in this case, the microgripper 221 can be driven by the stacked type piezoelectric element unit 225 provided on the fixed gripping section 222 of the microgripper 221, the insertion section of the treating unit can be narrowed as in the case of the first embodiment when being compared with the case where the movable gripping section 224 of the microgripper 221 is opened and closed by the operation wire. It is also possible to more accurately operate the microgripper 221.

Figure 23:
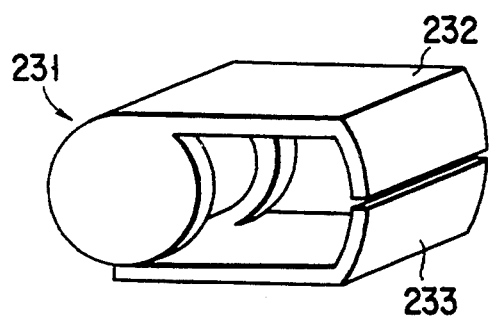
FIG. 23 is a perspective view showing a major part in an eleventh embodiment of the present invention.
Figure 24:
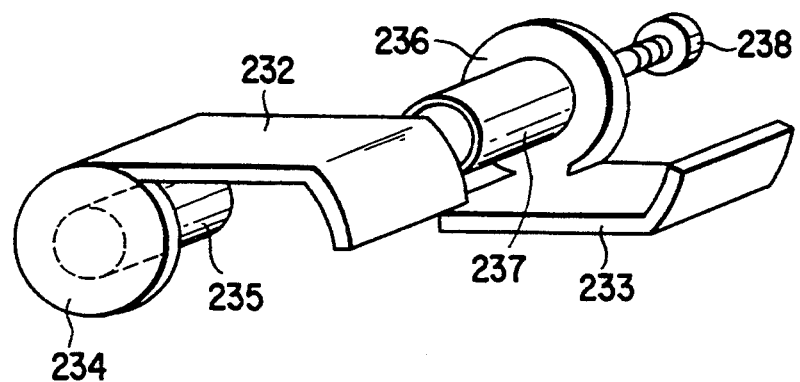
FIG. 24 is an exploded view of the major part shown in FIG. 23.

FIGS. 23 and 24 show an eleventh embodiment of the present invention. In this embodiment, a fixed gripping section 232 and movable gripping section 233 are provided in a microgripper 231 of the embodiment. The movable gripping section 233 is rotatably mounted relative to the fixed gripping section 232.

A substantially circular coupling frame 234 is formed on one side of the base end of the fixed gripping section 232 and a substantially cylindrical stator 235 for an ultrasonic motor is connected at one end to the coupling frame 234.

A substantially circular coupling frame 236 is provided on one side of the base end of the movable gripping section 233 and a substantially cylindrical rotor 273 for the ultrasonic motor is connected at one end to the coupling frame 236.

The stator 235 of the fixed gripping section 232 is inserted into the rotor 237 of the movable gripping section 233 and, in this state, both are firmly fixed together by a fastening screw 238. Thus the annular ultrasonic motor is provided by the mating sections of the stator 235 and rotator 237.

The microgripper 231 can be driven by the annular ultrasonic motor, thus obtaining the same advantage as in the first embodiment.

FIGS. 25 and 26 show a twelfth embodiment of the present invention. A first, substantially L-shaped frame 242 and second, substantially plate-like frame 243 are provided in a microgripper 241 of this embodiment.

An opening 245 is provided between a bent section 244 provided on the forward end side of the fist frame 242 and the forward end of the second frame 243 so as to grip a target. Further, a piston member 246 and linear type ultrasonic motor 247 are mounted on the second frame 243.

In this case, the piston member 248 has a projection 248 at a near-end side and the linear type ultrasonic motor 247 has an insertion hole 249 through which the projection 248 extends. In use of the microgripper 241, a target or an object of interest, such as a gallstone 250, can be trapped at the opening 245 between the bent portion 244 of the first frame 242 and the forward end of the second frame 243 and, through the driving of the linear type ultrasonic motor 247, the piston member 246 is operated, enabling it to be pushed toward the bent section 244 of the first frame 242 with the gallstone gripped therebetween.

Since, even in this case, the gallstone 250 can be gripped through the operation of the piston member 246 driven by the motor 247, it is possible to obtain the same merit as in the first embodiment of the present invention.

FIG. 27 shows a thirteenth embodiment of the present invention. In this embodiment, a piezoelectric element 252 is provided in each inner surface of the first frame 242 and second frame 243 and a linear type ultrasonic motor is provided by such first and second frames 242 and 243 per se. A piston member 251 is provided between the first frame 242 and the second frame 243 and moved back and forth by the linear type ultrasonic motor.

Even in this case, the piston member 251 is driven by the linear type ultrasonic motor in the microgripper 241 to enable the gallstone 250 to be gripped. By so doing it is possible to obtain the same advantage as the first embodiment.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A treating instrument for at least medical or industrial treatment, comprising:
   an insertion section insertable into a cavity to be treated, the insertion section having a distal end and an operator-side end;
   a treating unit provided at the distal end of the insertion section;
   an operation member provided on the treating unit and movable between a standby position and an operative position to treat a target region in the cavity;
   drive means including:
      a direct action type actuator means mounted to one of (i) an end portion of the distal end of the insertion section and (ii) the treating unit, for directly applying a linear pushing force to the operation member; and
      converting means for converting said linear pushing force to a moving force for moving the operation member between the standby position and the operative position; and
   means provided on the operator-side end of the insertion section, for outputting a control signal for controlling an operation of the drive means for thereby controlling said pushing force; and
   wherein:
   the insertion section includes a flexibly bendable multiarticulated structure, and an end capable of being disposed proximal to the target region in the cavity;
   the treating unit comprises one gripper including a flexible sheath having a forward end, a fixed frame secured to the forward end of the sheath and having a forward end, a first gripping member fixed to the forward end of the fixed frame, and a second gripping member having a rotation shaft on the forward end of the fixed frame, rotatably connected to the forward end of the fixed frame and serving as the operation member which is opened or closed relative to the first gripping member;
   the direct action type actuator means of the drive means and the means for converting said pushing force move the second gripping member of the treating unit between opened and closed positions relative to the first gripping member;
   the direct action type actuator means comprises a pair of piezoelectric units, each piezoelectric unit being formed of a plurality of stacked piezoelectric elements which are stacked in their thickness directions, each of the piezoelectric elements of a stack being displaceable so as to be extended in a thickness direction thereof upon conduction of electrical current;
   the converting means comprises a coupling frame formed on a base end of the second gripping member, a friction member fixed to the back end of the coupling frame, the pair of piezoelectric units being fixed at one end side thereof, to a base end of the coupling frame, contacting members extending in an eccentric position toward the friction member and positioned relative to the rotation shaft on another side of the piezoelectric units; and
   wherein, when electric current flows through one of the piezoelectric units, the stacked elements thereof extend in their thickness direction such that a corresponding contacting member is pushed against the friction member to close the second gripping member relative to the first gripping member and, when electric current flows through the other of the piezoelectric units, the stacked elements thereof extend in their thickness direction such that a corresponding contacting member is pushed against the friction member to open the second gripping member relative to the first gripping member.

2. The treating instrument according to claim 1, wherein:
   the direct action type actuator means is arranged for imparting a pushing force to a position eccentric with the rotation shaft so as to rotate the second gripping member.

* * * * *